(12) United States Patent
Joshi

(10) Patent No.: US 9,935,498 B2
(45) Date of Patent: Apr. 3, 2018

(54) COMMUNICATION EFFICIENCY WITH AN IMPLANTABLE MEDICAL DEVICE USING A CIRCULATOR AND A BACKSCATTER SIGNAL

(71) Applicant: CYBERONICS, INC., Houston, TX (US)

(72) Inventor: Himanshu Joshi, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 584 days.

(21) Appl. No.: 13/625,922

(22) Filed: Sep. 25, 2012

(65) Prior Publication Data

US 2014/0084855 A1 Mar. 27, 2014

(51) Int. Cl.
| | |
|---|---|
| H02J 7/00 | (2006.01) |
| H02J 50/12 | (2016.01) |
| H02J 50/70 | (2016.01) |
| H02J 50/80 | (2016.01) |
| H02J 50/90 | (2016.01) |
| H02J 7/02 | (2016.01) |
| H04B 5/00 | (2006.01) |
| A61B 5/00 | (2006.01) |
| A61N 1/378 | (2006.01) |
| A61N 1/372 | (2006.01) |
| H02J 5/00 | (2016.01) |

(52) U.S. Cl.
CPC ............ *H02J 50/12* (2016.02); *A61B 5/0031* (2013.01); *A61N 1/3787* (2013.01); *A61N 1/37223* (2013.01); *H02J 7/025* (2013.01); *H02J 50/70* (2016.02); *H02J 50/80* (2016.02); *H02J 50/90* (2016.02); *H04B 5/0031* (2013.01); *H04B 5/0037* (2013.01); *A61B 2560/0204* (2013.01); *H02J 5/005* (2013.01); *H04B 5/0075* (2013.01)

(58) Field of Classification Search
USPC ........................................................ 320/108
See application file for complete search history.

(56) References Cited

U.S. PATENT DOCUMENTS

| | | |
|---|---|---|
| 3,195,540 A | 7/1965 | Waller |
| 3,764,748 A | 10/1973 | Branch et al. |
| 4,014,346 A | 3/1977 | Brownlee et al. |
| (Continued) | | |

OTHER PUBLICATIONS

Lin, Tse-Yu et al., "Ultra-thin tag fabrication and sensing technique using third harmonic for implantable wireless sensors," Microwave Symposium Digest (MTT), 2011 IEEE MTT-S International, Jun. 5-10, 2011, Baltimore, MD., 4 pages.

(Continued)

*Primary Examiner* — Eric Lee
(74) *Attorney, Agent, or Firm* — Foley & Lardner LLP

(57) ABSTRACT

A device includes a primary antenna configured to communicate a signal to an antenna of an implantable medical device (IMD). A circulator is coupled to the primary antenna. The circulator enables the signal to pass from a transmitter to the primary antenna. The circulator also enables a backscatter signal from the IMD to pass from the primary antenna to a receiver. A processor coupled to the receiver. The processor configured to determine, based on the backscatter signal, an improved impedance value for a component of the IMD and/or an improved frequency for the signal communicated to the IMD, to improve communication efficiency of the signal to the IMD.

20 Claims, 9 Drawing Sheets

(56) References Cited

U.S. PATENT DOCUMENTS

| | | |
|---|---|---|
| 4,925,443 A | 5/1990 | Heilman et al. |
| 5,279,292 A | 1/1994 | Baumann et al. |
| 5,290,227 A | 3/1994 | Pasque |
| 5,350,413 A | 9/1994 | Miller |
| 5,411,537 A | 5/1995 | Munshi et al. |
| 5,569,156 A | 10/1996 | Mussivand |
| 5,591,217 A | 1/1997 | Barreras |
| 5,630,836 A | 5/1997 | Prem et al. |
| 5,676,162 A | 10/1997 | Larson, Jr. et al. |
| 5,676,651 A | 10/1997 | Larson, Jr. et al. |
| 5,690,693 A | 11/1997 | Wang et al. |
| 5,693,091 A | 12/1997 | Larson, Jr. et al. |
| 5,702,430 A | 12/1997 | Larson, Jr. et al. |
| 5,702,431 A | 12/1997 | Wang et al. |
| 5,704,891 A | 1/1998 | Mussivand |
| 5,713,939 A | 2/1998 | Nedungadi et al. |
| 5,722,930 A | 3/1998 | Larson, Jr. et al. |
| 5,733,313 A | 3/1998 | Barreras, Sr. et al. |
| 5,755,748 A | 5/1998 | Borza |
| 5,758,666 A | 6/1998 | Larson, Jr. et al. |
| 5,769,877 A | 6/1998 | Barreras |
| 5,807,397 A | 9/1998 | Barreras |
| 5,810,015 A | 9/1998 | Flaherty |
| 5,814,095 A | 9/1998 | Muller et al. |
| 5,879,375 A | 3/1999 | Larson, Jr. et al. |
| 5,945,762 A | 8/1999 | Chen et al. |
| 5,948,006 A | 9/1999 | Mann |
| 5,954,058 A | 9/1999 | Flaherty |
| 5,991,665 A | 11/1999 | Wang et al. |
| 5,995,874 A | 11/1999 | Borza |
| 6,052,624 A | 4/2000 | Mann |
| 6,058,330 A | 5/2000 | Borza |
| 6,067,474 A | 5/2000 | Schulman et al. |
| 6,067,991 A | 5/2000 | Forsell |
| 6,088,619 A | 7/2000 | Hein et al. |
| 6,092,531 A | 7/2000 | Chen et al. |
| 6,141,588 A | 10/2000 | Cox et al. |
| 6,164,284 A | 12/2000 | Schulman et al. |
| 6,166,518 A | 12/2000 | Echarri et al. |
| 6,185,452 B1 | 2/2001 | Schulman et al. |
| 6,205,359 B1 | 3/2001 | Boveja |
| 6,208,894 B1 | 3/2001 | Schulman et al. |
| 6,210,347 B1 | 4/2001 | Forsell |
| 6,212,431 B1 * | 4/2001 | Hahn ............... A61N 1/3787 607/61 |
| 6,227,204 B1 | 5/2001 | Baumann et al. |
| 6,240,316 B1 | 5/2001 | Richmond et al. |
| 6,240,318 B1 | 5/2001 | Phillips |
| 6,269,266 B1 | 7/2001 | Leysieffer |
| 6,272,382 B1 | 8/2001 | Faltys et al. |
| 6,275,737 B1 | 8/2001 | Mann |
| 6,278,258 B1 | 8/2001 | Echarri et al. |
| 6,308,101 B1 | 10/2001 | Faltys et al. |
| 6,315,721 B2 | 11/2001 | Schulman et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,331,744 B1 | 12/2001 | Chen et al. |
| 6,345,202 B2 | 2/2002 | Richmond et al. |
| 6,356,788 B2 | 3/2002 | Boveja |
| 6,366,814 B1 | 4/2002 | Boveja et al. |
| 6,368,592 B1 | 4/2002 | Colton et al. |
| 6,389,318 B1 | 5/2002 | Zarinetchi et al. |
| 6,392,386 B2 | 5/2002 | Schulmayr et al. |
| 6,393,325 B1 | 5/2002 | Mann et al. |
| 6,430,444 B1 | 8/2002 | Borza |
| 6,442,434 B1 | 8/2002 | Zarinetchi et al. |
| 6,445,162 B1 | 9/2002 | Mukainakano |
| 6,450,173 B1 | 9/2002 | Forsell |
| 6,450,946 B1 | 9/2002 | Forsell |
| 6,453,198 B1 | 9/2002 | Torgerson et al. |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,464,655 B1 | 10/2002 | Shahinpoor |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,496,733 B2 | 12/2002 | Zarinetchi et al. |
| 6,503,189 B1 | 1/2003 | Forsell |
| 6,505,074 B2 | 1/2003 | Boveja et al. |
| 6,505,077 B1 | 1/2003 | Kast et al. |
| 6,516,227 B1 | 2/2003 | Meadows et al. |
| 6,525,512 B2 | 2/2003 | Wuzik et al. |
| 6,531,847 B1 | 3/2003 | Tsukamoto et al. |
| 6,533,733 B1 | 3/2003 | Ericson et al. |
| 6,540,659 B1 | 4/2003 | Milbocker |
| 6,553,263 B1 | 4/2003 | Meadows et al. |
| 6,554,762 B2 | 4/2003 | Leysieffer |
| 6,564,102 B1 | 5/2003 | Boveja |
| 6,564,807 B1 | 5/2003 | Schulman et al. |
| 6,565,503 B2 | 5/2003 | Leysieffer et al. |
| 6,570,363 B2 | 5/2003 | Boberschmidt et al. |
| 6,575,894 B2 | 6/2003 | Leysieffer et al. |
| 6,586,912 B1 | 7/2003 | Tsukamoto et al. |
| 6,587,724 B2 | 7/2003 | Mann et al. |
| 6,592,512 B2 | 7/2003 | Stöckert et al. |
| 6,609,032 B1 | 8/2003 | Woods et al. |
| 6,611,715 B1 | 8/2003 | Boveja |
| 6,615,081 B1 | 9/2003 | Boveja |
| 6,620,094 B2 | 9/2003 | Miller |
| 6,629,923 B2 | 10/2003 | Leysieffer |
| 6,631,296 B1 | 10/2003 | Parramon et al. |
| 6,657,351 B2 | 12/2003 | Chen et al. |
| 6,664,763 B2 | 12/2003 | Echarri et al. |
| 6,668,191 B1 | 12/2003 | Boveja |
| 6,678,561 B2 | 1/2004 | Forsell |
| 6,695,885 B2 | 2/2004 | Schulman et al. |
| 6,697,674 B2 | 2/2004 | Leysieffer et al. |
| 6,709,385 B2 | 3/2004 | Forsell |
| 6,726,678 B1 | 4/2004 | Nelson et al. |
| 6,731,986 B2 | 5/2004 | Mann et al. |
| 6,736,770 B2 | 5/2004 | Leysieffer et al. |
| 6,745,077 B1 | 6/2004 | Griffith et al. |
| 6,807,445 B2 | 10/2004 | Baumann et al. |
| 6,850,803 B1 | 2/2005 | Jimenez et al. |
| 6,856,838 B2 | 2/2005 | Parramon et al. |
| 6,875,180 B2 | 4/2005 | Weiner et al. |
| 6,879,859 B1 | 4/2005 | Boveja |
| 6,891,353 B2 | 5/2005 | Tsukamoto et al. |
| 6,894,456 B2 | 5/2005 | Tsukamoto et al. |
| 6,895,280 B2 | 5/2005 | Meadows et al. |
| 6,901,290 B2 | 5/2005 | Foster et al. |
| 6,909,917 B2 | 6/2005 | Woods et al. |
| 6,915,165 B2 | 7/2005 | Forsell |
| 6,937,894 B1 | 8/2005 | Isaac et al. |
| 6,949,929 B2 | 9/2005 | Gray et al. |
| 6,954,674 B2 | 10/2005 | Connelly et al. |
| 6,979,351 B2 | 12/2005 | Forsell et al. |
| 7,001,427 B2 | 2/2006 | Aharoni et al. |
| 7,009,362 B2 | 3/2006 | Tsukamoto et al. |
| 7,011,624 B2 | 3/2006 | Forsell |
| 7,017,583 B2 | 3/2006 | Forsell |
| 7,062,330 B1 | 6/2006 | Boveja et al. |
| 7,062,331 B2 | 6/2006 | Zarinetchi et al. |
| 7,063,691 B2 | 6/2006 | Nelson et al. |
| 7,076,304 B2 | 7/2006 | Thompson |
| 7,076,307 B2 | 7/2006 | Boveja et al. |
| 7,107,103 B2 | 9/2006 | Schulman |
| 7,114,502 B2 | 10/2006 | Schulman et al. |
| 7,123,013 B2 | 10/2006 | Gray |
| 7,126,310 B1 | 10/2006 | Barron |
| 7,151,914 B2 | 12/2006 | Brewer |
| 7,155,291 B2 | 12/2006 | Zarinetchi et al. |
| 7,167,756 B1 | 1/2007 | Torgerson et al. |

(56) References Cited

U.S. PATENT DOCUMENTS

| | | |
|---|---|---|
| 7,177,690 B2 | 2/2007 | Woods et al. |
| 7,177,691 B2 | 2/2007 | Meadows et al. |
| 7,184,836 B1 | 2/2007 | Meadows et al. |
| 7,191,012 B2 | 3/2007 | Boveja et al. |
| 7,198,594 B2 | 4/2007 | Shahinpoor |
| 7,200,504 B1 | 4/2007 | Fister |
| 7,212,110 B1 | 5/2007 | Martin et |
| 7,212,864 B2 | 5/2007 | Wahlstrand et al. |
| 7,225,032 B2 | 5/2007 | Schmeling et al. |
| 7,226,442 B2 | 6/2007 | Sheppard et al. |
| 7,235,044 B2 | 6/2007 | Forsell |
| 7,239,918 B2 | 7/2007 | Strother et al. |
| 7,242,982 B2 | 7/2007 | Singhal et al. |
| 7,248,929 B2 | 7/2007 | Meadows et al. |
| 7,263,401 B2 | 8/2007 | Scott et al. |
| 7,283,867 B2 | 10/2007 | Strother et al. |
| 7,286,880 B2 | 10/2007 | Olson et al. |
| 7,286,881 B2 | 10/2007 | Schommer et al. |
| 7,295,878 B1 | 11/2007 | Meadows et al. |
| 7,317,947 B2 | 1/2008 | Wahlstrand et al. |
| 7,337,010 B2 | 2/2008 | Howard et al. |
| 7,367,938 B2 | 5/2008 | Forsell |
| 7,376,563 B2 | 5/2008 | Leysieffer et al. |
| 7,379,775 B2 | 5/2008 | Parramon et al. |
| 7,388,378 B2 | 6/2008 | Gray et al. |
| 7,392,089 B2 | 6/2008 | Wahlstrand et al. |
| 7,400,926 B2 | 7/2008 | Forsell |
| 7,426,445 B1 | 9/2008 | Fister |
| 7,444,184 B2 | 10/2008 | Boveja et al. |
| 7,460,911 B2 | 12/2008 | Cosendai et al. |
| 7,486,048 B2 | 2/2009 | Tsukamoto et al. |
| 7,496,404 B2 | 2/2009 | Meadows et al. |
| 7,499,753 B2 | 3/2009 | Forsell |
| 7,505,816 B2 | 3/2009 | Schmeling et al. |
| 7,513,257 B2 | 4/2009 | Schulman et al. |
| 7,515,967 B2 | 4/2009 | Phillips et al. |
| 7,529,586 B2 | 5/2009 | Wahlstrand et al. |
| 7,532,933 B2 | 5/2009 | Hastings et al. |
| 7,555,346 B1 | 6/2009 | Woods et al. |
| 7,592,776 B2 | 9/2009 | Tsukamoto et al. |
| 7,596,408 B2 | 9/2009 | Singhal et al. |
| 7,621,863 B2 | 11/2009 | Forsell |
| 7,621,878 B2 | 11/2009 | Ericson et al. |
| 7,635,541 B2 | 12/2009 | Scott et al. |
| 7,647,109 B2 | 1/2010 | Hastings et al. |
| 7,648,455 B2 | 1/2010 | Forsell |
| 7,666,132 B2 | 2/2010 | Forsell |
| 7,671,594 B2 | 3/2010 | Gray |
| 7,682,745 B2 | 3/2010 | Howard et al. |
| 7,684,867 B2 | 3/2010 | Jaax et al. |
| 7,720,546 B2 | 5/2010 | Ginggen et al. |
| 7,727,277 B2 | 6/2010 | Aharoni et al. |
| 7,729,777 B2 | 6/2010 | Gray et al. |
| 7,736,390 B2 | 6/2010 | Aharoni et al. |
| 7,738,965 B2 | 6/2010 | Phillips et al. |
| 7,765,003 B2 | 7/2010 | Peters et al. |
| 7,769,462 B2 | 8/2010 | Meadows et al. |
| 7,774,069 B2 | 8/2010 | Olson et al. |
| 7,776,087 B2 | 8/2010 | Aharoni et al. |
| 7,782,190 B1 | 8/2010 | Martin et al. |
| 7,792,588 B2 | 9/2010 | Harding et al. |
| 7,801,615 B2 | 9/2010 | Meadows et al. |
| 7,807,299 B2 | 10/2010 | Howard et al. |
| 7,811,705 B2 | 10/2010 | Scott et al. |
| 7,813,809 B2 | 10/2010 | Strother et al. |
| 7,818,068 B2 | 10/2010 | Meadows et al. |
| 7,839,146 B2 | 11/2010 | Gray |
| 7,848,814 B2 | 12/2010 | Torgerson et al. |
| 7,848,817 B2 | 12/2010 | Janzig et al. |
| 7,865,245 B2 | 1/2011 | Torgerson et al. |
| 7,875,389 B2 | 1/2011 | Scott et al. |
| 7,881,796 B2 | 2/2011 | Scott et al. |
| 7,894,913 B2 | 2/2011 | Boggs, II et al. |
| 7,904,170 B2 | 3/2011 | Harding et al. |
| 7,917,213 B2 | 3/2011 | Bulkes et al. |
| 7,925,357 B2 | 4/2011 | Phillips et al. |
| 7,927,742 B2 | 4/2011 | Scott et al. |
| 7,930,030 B2 | 4/2011 | Woods et al. |
| 7,931,582 B2 | 4/2011 | Forsell |
| 7,932,696 B2 | 4/2011 | Peterson |
| 7,945,334 B2 | 5/2011 | Jimenez et al. |
| 7,952,349 B2 | 5/2011 | Huang et al. |
| 7,962,211 B2 | 6/2011 | Torgerson et al. |
| 7,988,616 B2 | 8/2011 | Forsell |
| 8,005,547 B2 | 8/2011 | Forsberg et al. |
| 8,010,205 B2 | 8/2011 | Rahman et al. |
| RE42,682 E | 9/2011 | Barreras, Sr. et al. |
| 8,024,047 B2 | 9/2011 | Olson et al. |
| 8,036,736 B2 | 10/2011 | Snyder et al. |
| 8,044,635 B2 | 10/2011 | Peterson |
| 8,086,313 B2 | 12/2011 | Singhal et al. |
| 8,096,938 B2 | 1/2012 | Forsell |
| 8,096,939 B2 | 1/2012 | Forsell |
| 8,105,714 B2 | 1/2012 | Schmidt et al. |
| 8,115,448 B2 | 2/2012 | John |
| 8,126,558 B2 | 2/2012 | Forsell |
| 8,140,168 B2 | 3/2012 | Olson et al. |
| 8,147,543 B2 | 4/2012 | Forsell |
| 8,150,529 B2 | 4/2012 | Snell et al. |
| 8,155,752 B2 | 4/2012 | Aghassian et al. |
| 8,162,924 B2 | 4/2012 | Boyden et al. |
| 8,165,663 B2 | 4/2012 | Hyde et al. |
| 8,165,678 B2 | 4/2012 | Forsberg et al. |
| 8,165,692 B2 | 4/2012 | Strother et al. |
| 8,170,681 B2 | 5/2012 | Jimenez et al. |
| 8,175,716 B2 | 5/2012 | Rahman et al. |
| 8,195,304 B2 | 6/2012 | Strother et al. |
| 8,299,652 B2 * | 10/2012 | Sample .................. H02J 5/005 307/104 |
| 2003/0171792 A1 | 9/2003 | Zarinetchi et al. |
| 2004/0172102 A1 | 9/2004 | Leysieffer et al. |
| 2004/0173221 A1 | 9/2004 | Singhal et al. |
| 2004/0176815 A1 | 9/2004 | Janzig et al. |
| 2004/0176818 A1 | 9/2004 | Wahlstrand et al. |
| 2005/0075693 A1 | 4/2005 | Toy et al. |
| 2005/0104577 A1 | 5/2005 | Matei et al. |
| 2005/0113887 A1 | 5/2005 | Bauhahn et al. |
| 2006/0183965 A1 | 8/2006 | Kasic |
| 2007/0015959 A1 | 1/2007 | Forsell |
| 2007/0060968 A1 | 3/2007 | Strother et al. |
| 2007/0060980 A1 | 3/2007 | Strother et al. |
| 2007/0066995 A1 | 3/2007 | Strother et al. |
| 2007/0073099 A1 | 3/2007 | Forsell |
| 2007/0150037 A1 | 6/2007 | Hastings et al. |
| 2007/0150038 A1 | 6/2007 | Hastings et al. |
| 2007/0208390 A1 | 9/2007 | Von Arx et al. |
| 2007/0232848 A1 | 10/2007 | Forsell |
| 2007/0233019 A1 | 10/2007 | Forsell |
| 2007/0239224 A1 | 10/2007 | Bennett et al. |
| 2007/0270921 A1 | 11/2007 | Strother et al. |
| 2007/0279020 A1 | 12/2007 | Mozzi et al. |
| 2007/0293914 A1 | 12/2007 | Woods et al. |
| 2008/0020278 A1 | 1/2008 | Schmidt et al. |
| 2008/0021505 A1 | 1/2008 | Hastings et al. |
| 2008/0027500 A1 | 1/2008 | Chen |
| 2008/0044728 A1 | 2/2008 | Schmidt et al. |
| 2008/0051854 A1 | 2/2008 | Bulkes et al. |
| 2008/0092911 A1 | 4/2008 | Schulman et al. |
| 2008/0109054 A1 | 5/2008 | Hastings et al. |
| 2008/0161874 A1 | 7/2008 | Bennett et al. |
| 2008/0177353 A1 | 7/2008 | Hirota et al. |
| 2008/0221555 A1 | 9/2008 | Sheppard et al. |
| 2008/0275296 A1 | 11/2008 | Forsell |
| 2008/0300660 A1 | 12/2008 | John |
| 2009/0018599 A1 | 1/2009 | Hastings et al. |
| 2009/0024179 A1 | 1/2009 | Dronov |
| 2009/0048524 A1 | 2/2009 | Wildau et al. |
| 2009/0054725 A1 | 2/2009 | Forsell |
| 2009/0093713 A1 | 4/2009 | Hyde et al. |
| 2009/0093728 A1 | 4/2009 | Hyde et al. |
| 2009/0112291 A1 | 4/2009 | Wahlstrand et al. |
| 2009/0163964 A1 | 6/2009 | Boyden et al. |
| 2009/0163965 A1 | 6/2009 | Boyden et al. |
| 2009/0163977 A1 | 6/2009 | Boyden et al. |

(56) References Cited

U.S. PATENT DOCUMENTS

| | | |
|---|---|---|
| 2009/0177139 A1 | 7/2009 | Boyden et al. |
| 2009/0177254 A1 | 7/2009 | Boyden et al. |
| 2009/0182388 A1 | 7/2009 | Von Arx et al. |
| 2009/0216296 A1 | 8/2009 | Meskens et al. |
| 2009/0228077 A1 | 9/2009 | Ginggen et al. |
| 2009/0228078 A1 | 9/2009 | Zhang et al. |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248109 A1 | 10/2009 | Forsell |
| 2009/0250068 A1 | 10/2009 | Forsell |
| 2009/0254106 A1 | 10/2009 | Forsell |
| 2009/0274849 A1 | 11/2009 | Scott et al. |
| 2009/0292336 A1 | 11/2009 | Nishida et al. |
| 2010/0007307 A1 | 1/2010 | Baarman et al. |
| 2010/0063347 A1 | 3/2010 | Yomtov et al. |
| 2010/0106028 A1 | 4/2010 | Penner et al. |
| 2010/0106223 A1 | 4/2010 | Grevious et al. |
| 2010/0137948 A1 | 6/2010 | Aghassian et al. |
| 2010/0145139 A1 | 6/2010 | Forsell |
| 2010/0145412 A1 | 6/2010 | Boyden et al. |
| 2010/0174346 A1 | 7/2010 | Boyden et al. |
| 2010/0210955 A1 | 8/2010 | Forsell |
| 2010/0211091 A1 | 8/2010 | Forsell |
| 2010/0211092 A1 | 8/2010 | Forsell |
| 2010/0217067 A1 | 8/2010 | Forsell |
| 2010/0217295 A1 | 8/2010 | Forsell |
| 2010/0222847 A1 | 9/2010 | Goetz |
| 2010/0228079 A1 | 9/2010 | Forsell |
| 2010/0234792 A1 | 9/2010 | Dacey, Jr. et al. |
| 2010/0234793 A1 | 9/2010 | Dacey, Jr. et al. |
| 2010/0240017 A1 | 9/2010 | Dacey, Jr. et al. |
| 2010/0241048 A1 | 9/2010 | Dacey, Jr. et al. |
| 2010/0241049 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0241054 A1 | 9/2010 | Dacey, Jr. et al. |
| 2010/0241055 A1 | 9/2010 | Dacey, Jr. et al. |
| 2010/0249692 A1 | 9/2010 | Dacey, Jr. et al. |
| 2010/0249888 A1 | 9/2010 | Glenn et al. |
| 2010/0274310 A1 | 10/2010 | Boggs, II et al. |
| 2010/0292629 A1 | 11/2010 | Dacey, Jr. et al. |
| 2010/0305662 A1 | 12/2010 | Ozawa et al. |
| 2010/0305663 A1 | 12/2010 | Aghassian |
| 2010/0316898 A1 | 12/2010 | Howard et al. |
| 2010/0324354 A1 | 12/2010 | Peters et al. |
| 2010/0331917 A1 | 12/2010 | DiGiore et al. |
| 2010/0331918 A1 | 12/2010 | DiGiore et al. |
| 2010/0331919 A1 | 12/2010 | DiGiore et al. |
| 2010/0331920 A1 | 12/2010 | DiGiore et al. |
| 2011/0004269 A1 | 1/2011 | Strother et al. |
| 2011/0015473 A1 | 1/2011 | Forsell |
| 2011/0015474 A1 | 1/2011 | Forsell |
| 2011/0022125 A1 | 1/2011 | Olson et al. |
| 2011/0040143 A1 | 2/2011 | Forsell |
| 2011/0046699 A1 | 2/2011 | Mazanec |
| 2011/0046730 A1 | 2/2011 | Meskens |
| 2011/0054563 A1 | 3/2011 | Janzig et al. |
| 2011/0060386 A1 | 3/2011 | Woods et al. |
| 2011/0066254 A1 | 3/2011 | Forsell |
| 2011/0077720 A1 | 3/2011 | Torgerson et al. |
| 2011/0087337 A1 | 4/2011 | Forsell |
| 2011/0144468 A1 | 6/2011 | Boggs, II et al. |
| 2011/0144566 A1 | 6/2011 | Dacey, Jr. et al. |
| 2011/0152750 A1 | 6/2011 | Dacey, Jr. et al. |
| 2011/0152751 A1 | 6/2011 | Dacey, Jr. et al. |
| 2011/0152752 A1 | 6/2011 | Dacey, Jr. et al. |
| 2011/0152789 A1 | 6/2011 | Dacey, Jr. et al. |
| 2011/0152790 A1 | 6/2011 | Dacey, Jr. et al. |
| 2011/0152978 A1 | 6/2011 | Dacey, Jr. et al. |
| 2011/0156635 A1* | 6/2011 | Hong .................. H02J 5/005 320/107 |
| 2011/0160643 A1 | 6/2011 | Dacey, Jr. et al. |
| 2011/0160644 A1 | 6/2011 | Dacey, Jr. et al. |
| 2011/0160681 A1 | 6/2011 | Dacey, Jr. et al. |
| 2011/0166630 A1 | 7/2011 | Phillips et al. |
| 2011/0175568 A1 | 7/2011 | Leijssen et al. |
| 2011/0178576 A1 | 7/2011 | Aghassian |
| 2011/0184230 A1 | 7/2011 | Forsell et al. |
| 2011/0192402 A1 | 8/2011 | Forsell |
| 2011/0208021 A1 | 8/2011 | Goodall et al. |
| 2011/0208023 A1 | 8/2011 | Goodall et al. |
| 2011/0208026 A1 | 8/2011 | Goodall et al. |
| 2011/0208231 A1 | 8/2011 | Forsell |
| 2011/0218382 A1 | 9/2011 | Orejola |
| 2011/0230930 A1 | 9/2011 | Forsell |
| 2011/0230935 A1 | 9/2011 | Zdeblick |
| 2011/0234155 A1 | 9/2011 | Chen et al. |
| 2011/0273138 A1 | 11/2011 | Baarman et al. |
| 2011/0275912 A1 | 11/2011 | Boyden et al. |
| 2011/0280426 A1 | 11/2011 | Bachler |
| 2011/0281148 A1 | 11/2011 | Scott et al. |
| 2011/0282134 A1 | 11/2011 | Forsell |
| 2011/0288499 A1 | 11/2011 | Forsell |
| 2011/0295088 A1 | 12/2011 | Boyden et al. |
| 2011/0295089 A1 | 12/2011 | Boyden et al. |
| 2011/0295090 A1 | 12/2011 | Boyden et al. |
| 2011/0295159 A1 | 12/2011 | Shachar |
| 2011/0301667 A1 | 12/2011 | Olson et al. |
| 2011/0301669 A1 | 12/2011 | Olson et al. |
| 2011/0319703 A1 | 12/2011 | Wiskerke |
| 2011/0319785 A1 | 12/2011 | Snyder et al. |
| 2012/0007441 A1 | 1/2012 | John |
| 2012/0010481 A1 | 1/2012 | Goodall et al. |
| 2012/0012630 A1 | 1/2012 | Lui et al. |
| 2012/0019201 A1 | 1/2012 | Peterson |
| 2012/0032522 A1* | 2/2012 | Schatz et al. .................. 307/104 |
| 2012/0041285 A1 | 2/2012 | Goodall et al. |
| 2012/0041286 A1 | 2/2012 | Goodall et al. |
| 2012/0041287 A1 | 2/2012 | Goodall et al. |
| 2012/0041515 A1 | 2/2012 | Meskens et al. |
| 2012/0046712 A1 | 2/2012 | Woods et al. |
| 2012/0053657 A1 | 3/2012 | Parker et al. |
| 2012/0101874 A1 | 4/2012 | Ben-Haim et al. |
| 2012/0123505 A1 | 5/2012 | Kothandaraman |
| 2012/0130448 A1 | 5/2012 | Wood et al. |
| 2012/0139485 A1 | 6/2012 | Olson et al. |

OTHER PUBLICATIONS

Nikitin, Pavel V. et al, "Theory and Measurement of Backscattering From RFID Tags," Antennas and Propagation Magazine, IEEE, vol. 48, No. 6, pp. 212-218, Dec. 2006.

Jang, Byung-Jun "Hardware Design and Deployment Issues in UHF RFID Systems," 2010, 12 pages, Found at: http://www.intechopen.com/books/radio-frequency-identification-fundamentals-and-applications-design-methods-and-solutions/hardware-design-and-deployment-issues-in-uhf-rfid-systems.

* cited by examiner

US 9,935,498 B2

COMMUNICATION EFFICIENCY WITH AN IMPLANTABLE MEDICAL DEVICE USING A CIRCULATOR AND A BACKSCATTER SIGNAL

FIELD OF THE DISCLOSURE

The present disclosure is generally related to charging, and communicating with, implantable medical devices.

BACKGROUND

Powering and communicating with implantable medical devices can be problematic. Many implantable medical devices include a battery. If the battery is rechargeable, the implantable medical device may include charging components to receive power from an external source to recharge the battery. For example, the implantable medical device may include a coil that is operative to inductively couple with an external coil. Providing power via inductive coupling may require that the coil of the implantable medical device and the external coil be relatively close to one another (e.g., within a distance over which a magnetic field is relatively strong). Further, inductive coupling may be less efficient when the coil of the implantable medical device and the external coil are not aligned or oriented properly. Further, component value variations in implantable medical device circuitry and variations in tissue properties from patient to patient affect the communication efficiency of implantable medical devices.

SUMMARY

A device may be used to charge or communicate with an implantable medical device (IMD) that is implanted within tissue of a patient. For example, a primary antenna of the device may transmit a charging signal and/or a communication signal that is received by an antenna of the IMD. One of more components of the IMD may generate a backscatter signal in response to the signal. For example, one or more circuit components (e.g., diodes) may be used to generate a direct-current signal from the charging signal. The one or more components may generate the backscatter signal while generating the direct-current signal from the charging signal. In another example, impedance mismatch between the antenna and other components of the IMD may generate the backscatter signal in response to the charging and/or communication signal. The backscatter signal may be used to determine information related to the IMD. For example, the backscatter signal may convey information related to a charge state of a charge storage element, such as a rechargeable battery, of the IMD. The backscatter signal may be detected and processed to extract and/or estimate the information related to the IMD.

A particular embodiment relates to a device that includes a primary antenna configured to communicate a signal to an antenna of an implantable medical device. A circulator is coupled to the primary antenna. The circulator enables the signal to pass from a transmitter to the primary antenna. The circulator also enables a backscatter signal from the implantable medical device to pass from the primary antenna to a receiver. A processor is coupled to the receiver and is configured to determine, based on the backscatter signal, an improved impedance value for a component of the implantable medical device and/or an improved frequency for the signal communicated to the implantable medical device, to improve communication efficiency of the signal to the implantable medical device.

Another particular embodiment relates to a method that includes generating a signal at a transmitter of a device and applying the signal to a primary antenna of the device via a circulator. The method further includes communicating the signal to an antenna of an implantable medical device. The method further includes receiving, at the primary antenna, a backscatter signal generated by a circuit component of the implantable medical device responsive to the signal and providing the backscatter signal to a receiver of the device via the circulator. The method further includes determining, based on the backscatter signal, an improved impedance value for a component of the implantable medical device and/or an improved frequency for the signal communicated to the implantable medical device, to improve communication efficiency of the signal to the implantable medical device.

Another particular embodiment relates to an apparatus that includes means for generating a signal at a device and means for communicating the signal to an antenna of an implantable medical device. The apparatus also includes means for receiving a backscatter signal generated by a circuit component of the implantable medical device responsive to the signal. The apparatus further includes means for processing the backscatter signal and determining, based on the backscatter signal, an improved impedance value for a component of the implantable medical device and/or an improved frequency for the signal communicated to the implantable medical device, to improve communication efficiency of the signal to the implantable medical device.

BRIEF DESCRIPTION OF THE DRAWINGS

The disclosure will become more fully understood from the following detailed description, taken in conjunction with the accompanying drawings.

DETAILED DESCRIPTION

Figure 1:
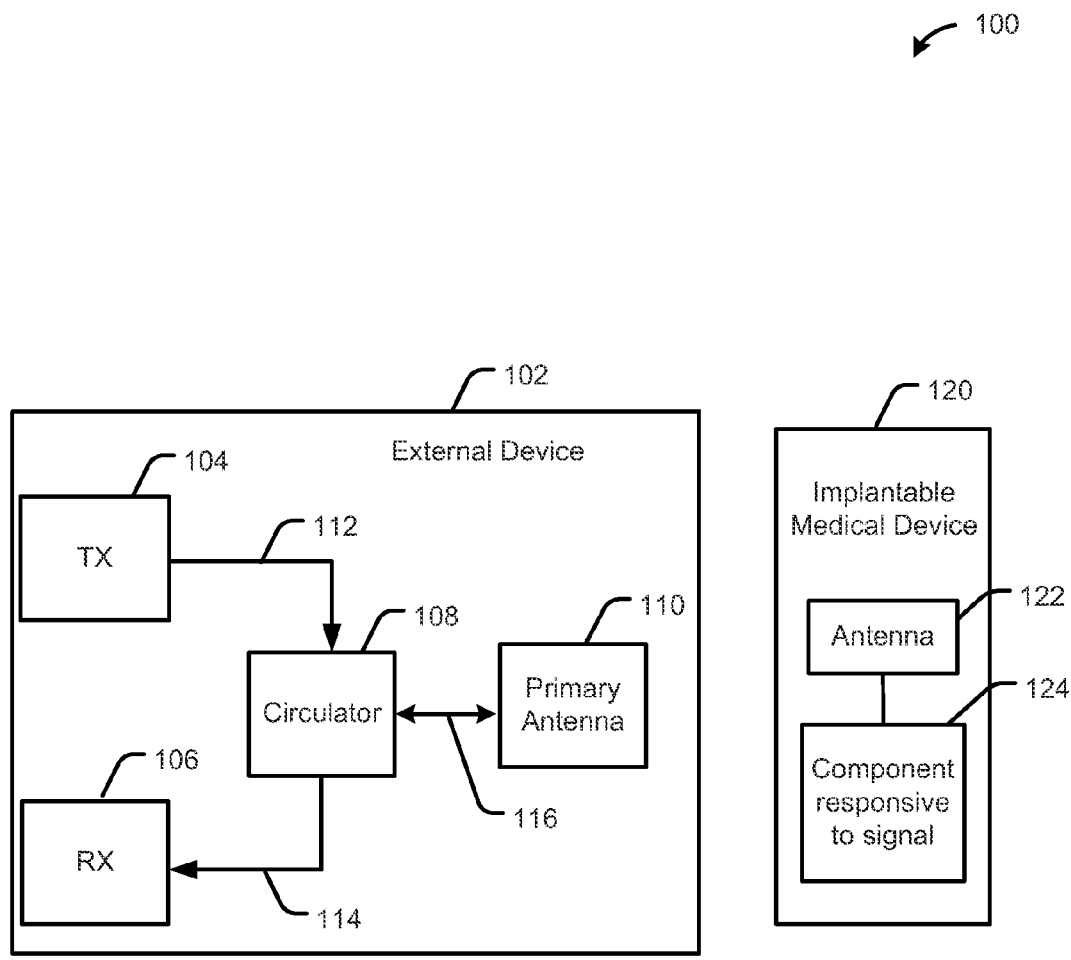
FIG. 1 is a block diagram of a system including an external device and an implantable medical device according to a first exemplary embodiment.

Referring to FIG. 1, a block diagram of a system 100 including an external device 102 and an implantable medical device (IMD) 120 is shown according to a particular embodiment. The external device 102 is configured to send a signal to the IMD 120 and to receive a backscatter signal from the IMD 120. The IMD 120 is configured to generate the backscatter signal responsive to the signal from the external device 102.

The external device 102 includes a transmitter 104, a receiver 106, a circulator 108, and a primary antenna 110. The transmitter 104 is coupled to the circulator 108 via a line 112. The transmitter 104 may send the signal to the circulator 108 via the line 112. The receiver 106 is coupled to the circulator 108 via a line 114. The receiver 106 may receive the backscatter signal from the circulator 108 via the line 114. The circulator 108 is coupled to the primary antenna 110. The circulator 108 enables the signal to pass from the transmitter 104 to the primary antenna 110. The circulator 108 also enables the backscatter signal from the IMD 120 to pass from the primary antenna 110 to the receiver 106. The circulator 108 is a multiport device that allows a signal entering at one port of the device to pass primarily to a next port of the device in a rotation. To illustrate, the circulator 108 allows the signal received at a first port coupled to the transmitter 104 to pass to a second port coupled to the primary antenna 110, but blocks all or most of the signal received at the first port from passing to a third port coupled to the receiver 106. The circulator 108 also allows a second signal (e.g., the backscatter signal) received at the second port coupled to the primary antenna 110 to pass to the third port coupled to the receiver 106, but blocks all or most of the second signal received at the second port from passing to the first port coupled to the transmitter 104. Thus, the circulator 108 may enable simultaneous or concurrent transmission of the signal and receipt of the backscatter signal. The circulator 108 may allow a relatively small portion of the signal to pass to the receiver 106 as a leakage signal. However, the leakage signal may be of sufficiently low power that the backscatter signal can be detected by the receiver 106.

The IMD 120 includes the antenna 122 and a component 124 that is responsive to the signal. The antenna 122 is coupled to the component 124. The component 124 that is responsive to the signal may include a circuit element or a set of circuit elements that generate the backscatter signal responsive to the signal. In addition to generating the backscatter signal, the component 124 that is responsive to the signal may perform other functions of the IMD 120. For example, the component 124 may include or be included within a matching network, a charge storage component, or another component of the IMD 120.

During operation, the transmitter 104 may provide the signal to the circulator 108 via the line 112. The circulator 108 may provide the signal to the primary antenna 110. The primary antenna 110 may radiatively transfer the signal to the antenna 122 of the IMD 120. The antenna 122 may provide the signal to the component 124. The component 124 may perform a function of the IMD 120 using, based on, or responsive to the signal. The component 124 of the IMD 120 may also generate the backscatter signal responsive to the signal. For example, impedance mismatch between the antenna 122 and the component 124 may generate the backscatter signal when the signal is received. In another example, the component 124 may generate the backscatter signal by itself when the signal is received. To illustrate, the component 124 may include or be coupled to a circuit that includes one or more circuit elements that generate the backscatter signal. Examples of circuit elements that may generate the backscatter signal include diodes of a rectifier circuit. The antenna 122 may transmit the backscatter signal, which may be received by the primary antenna 110. The primary antenna 110 may transfer the backscatter signal to the circulator 108. The circulator 108 may pass the backscatter signal to the receiver 106 on the line 114. In a particular embodiment, the backscatter signal has the same frequency as the signal.

The backscatter signal may be processed to extract and/or estimate information regarding the IMD 120. For example, the receiver 106 may process the backscatter signal and/or pass the backscatter signal to another component for processing. To illustrate, the receiver 106 may pass the backscatter signal to a processor as is described with respect to FIG. 2. Alternatively, the receiver 106 may pass the backscatter signal or data descriptive of the backscatter signal to a processor (not shown) that is external to the external device 102. In a particular embodiment, the backscatter signal may be used to detect presence of the IMD 120 within tissue of a patient. In a particular embodiment, the backscatter signal may include, or may be used to deduce, information related to tuning of a matching network of the IMD 120. For example, a characteristic of the backscatter signal (such as a magnitude of the backscatter signal) may change as tuning of the matching network changes. In a particular embodiment, the backscatter signal may include, or may be used to deduce, information related to charging efficiency of a charge storage element (as described further with reference to FIG. 2). For example, a characteristic of the backscatter signal (such as a magnitude of the backscatter signal) may change as radiofrequency (RF) charging efficiency of the charge storage element changes. Thus, by measuring the characteristic of the backscatter signal, the charging efficiency of the charge storage element 222 may be inferred. In a particular embodiment, the backscatter signal may include, or may be used to deduce, information related to selecting a frequency for communication with the IMD 120 (as described in more detail with reference to FIG. 3). For example, the backscatter signal may be strongest when the signal received by the component 124 is strongest. That is, when the signal is communicated more efficiently to the component 124, the component 124 may generate a stronger backscatter signal. Thus, a frequency sweep of available communication channels may be performed by the transmitter 104. The receiver 106 may receive a backscatter signal corresponding to each channel. A channel may be selected that corresponds to a strongest backscatter signal received by the receiver.

Use of the backscatter signal to extract and/or estimate information about the IMD 120 may enable determination of the information without the IMD 120 using stored energy to generate and to send a signal to convey the information about the IMD 120 to the external device 102. Thus, use of the backscatter signal may substantially reduce power consumption associated with generating and sending a signal to the external device 102 to convey the information about the IMD 120.

Figure 2:
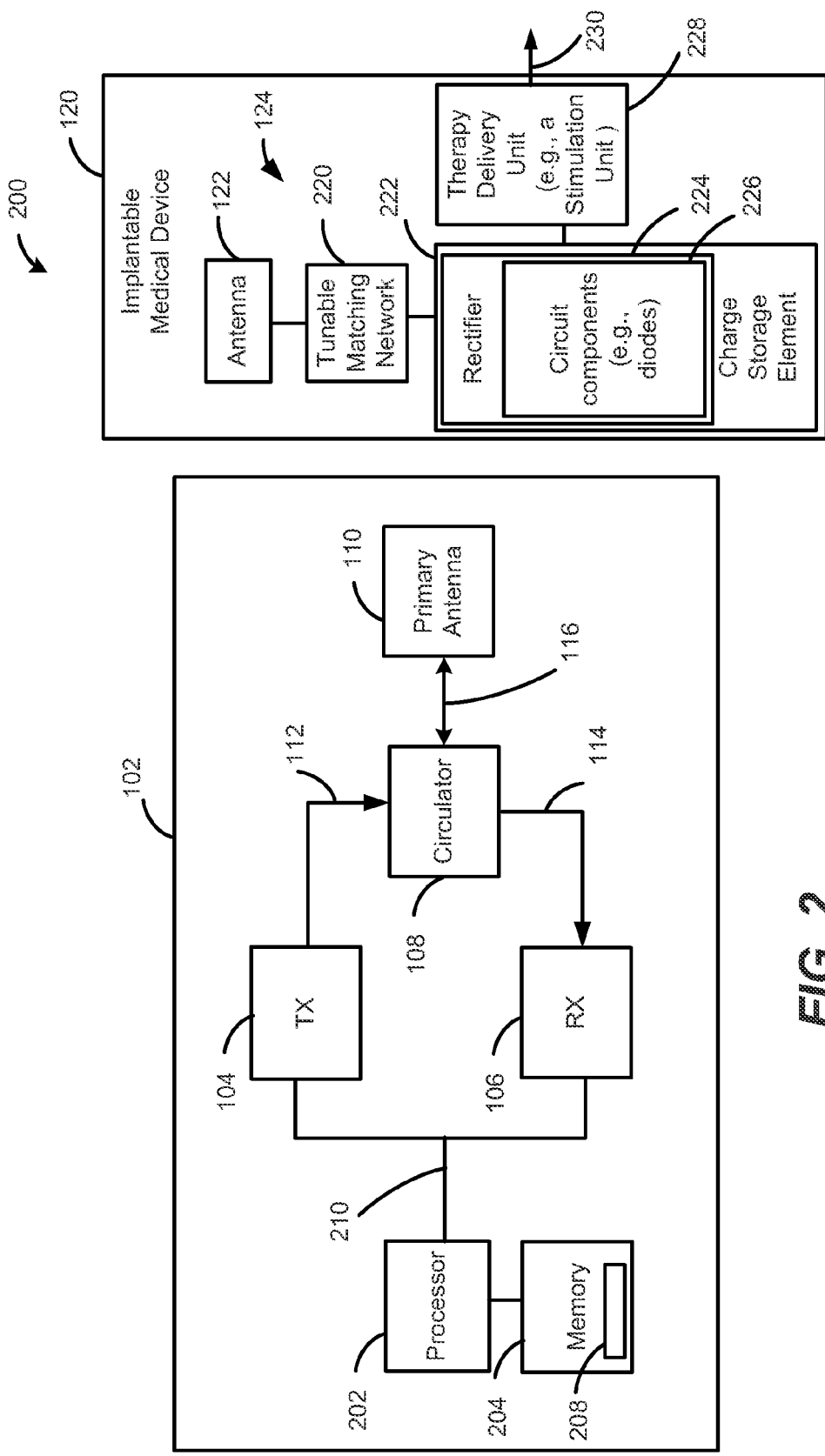
FIG. 2 is a block diagram of a system including the external device and the implantable medical device according to a second exemplary embodiment.

Referring to FIG. 2, a block diagram of a system 200 including the external device 102 and the implantable medical device (IMD) 120 is shown according to another particular embodiment. As in FIG. 1, the external device 102 includes the transmitter 104, the receiver 106, the circulator 108, and the primary antenna 110. In FIG. 2, the external device 102 also includes a processor 202 and a memory device 204 that includes instructions 208. For example, the memory device 204 may be a non-transitory machine-readable memory device. The memory device 204 may also store data. The memory device 204 is coupled to the processor 202. The processor 202 is coupled to the transmitter 104 and to the receiver 106 via a line 210. The transmitter 104 is coupled to the circulator 108 via the line 112, and the receiver 106 is coupled to the circulator 108 via the line 114. The circulator 108 is coupled to the primary antenna 110. Although the line 210, the line 112, and the line 114 are each shown as a single line, each of the line 210, the line 112, and the line 114 may represent multiple lines.

In a particular embodiment, the processor 202 may be configured to send a control signal to the transmitter 104. To illustrate, the processor 202 may send the control signal to the transmitter 104 via the line 210 to instruct the transmitter 104 to send the signal to the IMD 120. The processor 202 may also be configured to receive the backscatter signal from the receiver 106 via the line 210.

In a particular embodiment, the transmitter 104 may be configured to send the signal to the IMD 120 in response to the control signal from the processor 202. To illustrate, the transmitter 104 may send the signal to the IMD 120 via the circulator 108 via the line 112. The circulator 108 may be configured to pass the signal from the transmitter 104 to the primary antenna 110. The primary antenna 110 may be configured to radiatively communicate the signal to the antenna 122 of the IMD 120.

As in FIG. 1, the IMD 120 includes the antenna 122 and the component 124 that is responsive to the signal. In FIG. 2, the component 124 that is responsive to the signal may include, be included within, or correspond to a tunable matching network 220, a charge storage element 222, a rectifier 224, a circuit component 226 (such as a diode) of the rectifier 224, a therapy delivery unit 228 (e.g., a stimulation unit), or a combination thereof. The antenna 122 is coupled to the tunable matching network 220. The tunable matching network 220 is coupled to the charge storage element 222. The charge storage element 222 is coupled to the therapy delivery unit 228. The therapy delivery unit 228 may receive power to operate from the charge storage element 222.

In a particular embodiment, the tunable matching network 220 includes one or more capacitors, one or more inductors, one or more resistors, or any combination thereof. Impedance of the tunable matching network 220 may be adjusted to reduce signal power loss due to signal reflection that may be caused by impedance mismatch between the antenna 122 and the tunable matching network 220. To illustrate, the impedance of the tunable matching network 220 may be adjusted to provide improved impedance matching between the antenna 122, the tunable matching network 220, and one or more other components of the IMD 120, such as the charge storage element 222 or the therapy delivery unit 228. For example, the impedance of the tunable matching network 220 may be adjusted by adjusting a capacitance of one or more capacitors of the tunable matching network 220. Impedance mismatch may reduce charging efficiency at the charge storage element 222.

In a particular embodiment, a characteristic of the backscatter signal generated by the IMD 120 in response to the signal is related to the impedance matching between the antenna 122 and the tunable matching network 220. The processor 202 may be operable to determine, based on the characteristic of the backscatter signal whether the impedance matching between the antenna 122 and the tunable matching network 220 is within acceptable tolerances. When the impedance matching between the antenna 122 and the tunable matching network 220 is not within acceptable tolerances, the processor 202 may cause the transmitter 104 to send a tuning signal to the IMD 120. In response to the tuning signal, the impedance of the tunable matching network 220 may be modified. Thus, the backscatter signal may be used to improve charging efficiency of the charge storage element 222 by reducing impedance mismatch.

Alternately, or in addition, the processor 202 may cause the transmitter 104 to change a frequency of the signal, based on the backscatter signal, to reduce impedance mismatch at the IMD 120. For example, the processor 202 may cause the transmitter 104 to perform a frequency sweep of particular channels or frequency bands. The external device 102 may communicate with the IMD 120 using a selected channel of multiple available channels. The available channels may correspond to frequency bands that are authorized (e.g., by an appropriate governmental agency, such as the Federal Communication Commission in the United States) for use for medical device communications or other relatively low power, short range communications. The transmitter 104 may perform the frequency sweep by transmitting a first signal to the IMD 120 using a first channel of the available channels, subsequently transmitting a second signal to the IMD 120 using a second channel of the available channels, and so forth, through each of the available channels or through a subset of the available channels.

The receiver 106 may receive a backscatter signal corresponding to each signal transmitted during the frequency sweep (e.g., a first backscatter signal corresponding to the first signal, a second backscatter signal corresponding to the second signal, and so forth). The receiver 106 or the processor 202 may select a particular channel to be used to communicate with the IMD 120 based on the backscatter signals received during the frequency sweep. For example, a channel that corresponds to a backscatter signal that had a largest amplitude (e.g., a highest power backscatter signal) may be selected.

As explained above, the receiver 106 may receive a leakage signal corresponding to each signal transmitted during the frequency sweep. Thus, a signal detected may include the backscatter signal and the leakage signal. In this circumstance, the receiver 106 or the processor 202 may select a particular channel to be used to communicate with the IMD 120 that had a largest difference in amplitude between the backscatter signal and the leakage signal.

In a particular embodiment, the charge storage element 222 includes or is coupled to the rectifier 224. The rectifier 224 may be configured to rectify the signal from the external device 102 to generate a DC signal to charge the charge storage element 222. The rectifier 224 may include one or more circuit components 226 that generate a backscatter signal responsive to the signal. For example, the circuit components 226 may include one or more diodes or other circuit elements that are characterized by a non-linear current and voltage relationship. The rectifier 224 may also include one or more capacitors. The charge storage element 222 may include a rechargeable battery, a capacitor, another charge storage device, or a combination thereof. In a particular embodiment, circuit components coupled to the antenna 122 through the tunable matching network 220 may generate or contribute to generation of the backscatter signal. For example, the one or more diodes of the circuit components 226 may generate the backscatter signal.

In a particular embodiment, the therapy delivery unit 228 is configured to deliver therapy to a patient in which the implantable medical device 120 is implanted using power from the charge storage element 222. The therapy delivery unit 228 may deliver the therapy as one or more electrical signals applied to tissue of the patient, by delivery of a chemical to the patient, by other therapy delivery mechanisms, or a combination thereof. For example, the therapy delivery unit 228 may deliver the therapy as an electrical signal on a therapy line 230 that is coupled to one or more electrodes positioned proximate to target tissue of the patient. In another example, the therapy delivery unit 228 may include a drug delivery pump that is operable to deliver a drug to the patient.

In a particular embodiment, the backscatter signal has the same frequency as the signal transmitted by the external device 102. Thus, the receiver 106 may have difficulty distinguishing the backscatter signal from the signal. Accordingly, the primary antenna 110 of the external device 102 may be configured to receive the backscatter signal from the IMD 120 and to send the received backscatter signal to the receiver 106 via the circulator 108. The circulator 108 may be configured to pass the backscatter signal from the primary antenna 110 to the receiver 106. However, the circulator 108 may inhibit the signal from passing from the transmitter 104 to the receiver 106 (although a portion of the signal may pass from the transmitter 104 to the receiver 106 as a leakage signal). Thus, the circulator 108 enables the receiver 106 to distinguish the backscatter signal simultaneously or concurrently with transmission of the signal. The receiver 106 may send the backscatter signal to the processor 202. The backscatter signal may include or may be used to deduce information related to the IMD 120.

In a particular embodiment, to process the backscatter signal, the processor 202 may execute the instructions 208 stored in the memory device 204. For example, the processor 202 may be configured to estimate, based on the backscatter signal, impedance mismatch at the IMD 120. In another example, the processor 202 may be configured to select a channel for use to communicate with the IMD 120 based on the backscatter signal.

In a particular embodiment, when the signal is used as a charging signal, the processor 202 may be configured to estimate, based on the backscatter signal, charging efficiency of the charging signal with respect to the charge storage element 222. After estimating the charging efficiency of the charging signal, the processor 202 may adjust a frequency of the charging signal. For example, the processor 202 may send a control signal to the transmitter 104 to instruct the transmitter 104 to increase or to decrease the frequency of the charging signal. The processor 202 may also, or in the alternative, send a control signal to the transmitter 104 to instruct the transmitter 104 to set the frequency of the charging signal to a particular value.

In a particular embodiment, after estimating the charging efficiency of the charging signal, the processor 202 may cause the tunable matching network 220 of the IMD 120 to be adjusted to improve charging efficiency of the charging signal. For example, the processor 202 may generate an output signal to indicate whether the impedance of the tunable matching network 220 should be increased or decreased.

In a particular embodiment, the processor 202 may be configured to perform a frequency sweep of the charging signal to identify, based on the backscatter signal, a particular frequency associated with an improved charging efficiency relative to other frequencies of the charging signal. For example, the processor 202 may send a control signal to the transmitter 104 to instruct the transmitter 104 to send the charging signal at a specified frequency to the IMD 120. The processor 202 may repeatedly send control signals to the transmitter 104, each control signal indicating a different frequency of the charging signal. The processor 202 may process the backscatter signal from the IMD 120 corresponding to each frequency of the charging signal. After analyzing the backscatter signal corresponding to each frequency of the charge signal sent by the transmitter 104, the processor 202 may identify a particular frequency of the charging signal associated with an improved charging efficiency. In a particular embodiment, the processor 202 may perform the frequency sweep of the charging signal repeatedly during charging of the IMD 120. For example, as the charge state of the charge storage element 222 changes, recharging efficiency of the charging signal may change. Accordingly, the processor 202 may periodically or occasionally (e.g., based on a detected change in the charge state) repeat the frequency sweep of the charging signal to select a new frequency of the charging signal that is associated with improved charging efficiency.

In a particular embodiment, the processor 202 may detect presence of the IMD 120 that is near the external device 102 based on the backscatter signal. For example, the processor 202 may determine that the IMD 120 is within a particular distance of the external device 102 based on a signal strength of the backscatter signal. The processor 202 may also, or in the alternative, determine that the IMD 120 is not near the external device 102 if the processor 202 does not detect the backscatter signal or detects a weak backscatter signal. Based on the detected presence of the IMD 120, the processor 202 may generate an output signal to provide information about the distance of the external device 102 relative to the IMD 120. For example, the external device 102 may provide an indication to adjust a distance between the external device 102 and the IMD 120.

In a particular embodiment, the processor 202 may send a control signal to the transmitter 104 to instruct the transmitter 104 to cease generation of the charging signal, to terminate sending the charging signal to the primary antenna 110, or both in response to the backscatter signal. For example, the processor 202 may send the control signal to the transmitter 104 instructing the transmitter 104 to cease generation of the charging signal after estimating the charge state of the charge storage element 222 based on the backscatter signal. To illustrate, the backscatter signal may be used to determine information about charging efficiency of the charging signal. A portion of energy of the charging signal that does not result in charging of the charge storage element 222 may be lost as heat, which may increase a temperature of the IMD 120. To limit temperature rise of the IMD 120 to a level that is safe to be in contact with the tissue of the patient, the processor may cease application of the charging signal to the IMD 120 based on information related to temperature rise of the IMD 120, such as a time of application of the charging signal and the estimated efficiency of the charging signal. As another example, if the external device 102 sends the charging signal for a period of time without detecting the backscatter signal, this may be an indication that the IMD 120 is outside a range of the charging signal. Accordingly, the processor 202 may instruct the transmitter 104 to cease transmitting the charging signal.

During operation, the processor 202 may send a control signal to the transmitter 104 via the line 210. For example, the processor 202 may send the control signal to the transmitter 104 to instruct the transmitter 104 to send the signal (e.g., the charging signal, a communication signal, or both) to the IMD 120. The processor 202 may also indicate to the transmitter 104 a particular frequency the signal should have. The transmitter 104 may send the signal to the circulator 108 via the line 112. The circulator 108 may provide the signal to the primary antenna 110. The primary antenna 110 may radiatively transfer the signal to the antenna 122 of the IMD 120. The antenna 122 may provide the signal to the rectifier 224 of the charge storage element 222. For example, the antenna 122 may provide the signal to the rectifier 224 through the tunable matching network 220. The rectifier 224 may rectify the signal to generate the charging current. To illustrate, one or more diodes of the circuit components 226 may rectify the signal. The charge storage element 222 may be charged by the charging current from the rectifier 224.

The rectifier 224 may generate or contribute to generation of the backscatter signal. For example, the circuit components 226 of the rectifier 224 may generate the backscatter signal responsive to the signal. To illustrate, the one or more diodes of the circuit components 226 may generate the backscatter signal while generating the charging current based on the signal.

A signal strength or other characteristic of the backscatter signal may be related to a degree of impedance mismatch between the antenna 122 and the tunable matching network 220. For example, a relatively high impedance mismatch between the antenna 122 and the tunable matching network 220 may result in a weaker backscatter signal being generated by the rectifier 224. A relatively low impedance mismatch between the antenna 122 and the tunable matching network 220 may result in a stronger backscatter signal being generated by the rectifier 224.

A relatively high impedance mismatch between the antenna 122 and the tunable matching network 220 may result in a higher power loss of the signal than a relatively low impedance mismatch between the antenna 122 and the tunable matching network 220. Thus, the signal that reaches the rectifier 224 may have relatively lower power when the impedance mismatch between the antenna 122 and the tunable matching network 220 is relatively high. Similarly, the signal that reaches the rectifier 224 may have relatively higher power when the impedance mismatch between the antenna 122 and the tunable matching network 220 is relatively low. Accordingly, the one or more diodes of the circuit components 226 may generate a weaker backscatter signal when the impedance mismatch between the antenna 122 and the tunable matching network 220 is relatively high. Similarly, the one or more diodes of the non-linear circuit components 226 may generate a stronger backscatter signal when the impedance mismatch between the antenna 122 and the tunable matching network 220 is relatively low.

The backscatter signal generated by the rectifier 224 may travel to the antenna 122 through the tunable matching network 220. The antenna 122 may radiatively transfer the backscatter signal to the primary antenna 110 of the external device 102. The primary antenna 110 may send the backscatter signal from the antenna 122 to the circulator 108. The circulator 108 may pass the backscatter signal to the receiver 106 via the line 114. The receiver 106 may pass the backscatter signal to the processor 202.

The processor 202 may process the backscatter signal to extract and/or estimate information related to the IMD 120 based on a characteristic of the backscatter signal. For example, the processor 202 may process the backscatter signal based on the instructions 208 stored in the memory device 204. To illustrate, the processor 202 may process the backscatter signal to detect presence of the IMD 120. The processor 202 may also, or in the alternative, process the backscatter signal to estimate the charging efficiency of the signal with respect to the charge storage element 222. Based on the estimate of the charging efficiency of the charging signal, the processor 202 may adjust a frequency of the signal. For example, the processor 202 may send a control signal to the transmitter 104 instructing the transmitter 104 to change the frequency of the signal. Based on the estimate of the charging efficiency of the signal, the processor 202 may generate an output signal indicating whether the impedance of the tunable matching network 220 should be increased or decreased. The processor 202 may also, or in the alternative, control transmission of the signal to reduce heating of the IMD 120, to reduce recharge time (i.e., time for the charge storage element 222 to reach a particular charge state), to improve recharge efficiency, or a combination thereof.

Use of the backscatter signal to extract and/or estimate information about the IMD 120 may enable determination of the information without the IMD 120 using stored energy to generate and to send a radiofrequency signal to convey the information about the IMD 120 to the external device 102. Thus, use of the backscatter signal may substantially reduce power consumption associated with generating and sending a signal to the external device 102 to convey the information about the IMD 120.

Although FIG. 2 shows the processor 202 and the memory device 204 as part of the external device 102, in alternative embodiments, one or both of the processor 202 and the memory device 204 may be outside the external device 102. In addition, although FIG. 2 shows the tunable matching network 220 outside the charge storage element 222, in alternative embodiments, the tunable matching network 220 may be inside the charge storage element 222. Further, although FIG. 2 shows the rectifier 224 inside the charge storage element 222, in alternative embodiments, the rectifier 224 may be outside of the charge storage element 222.

Figure 3:
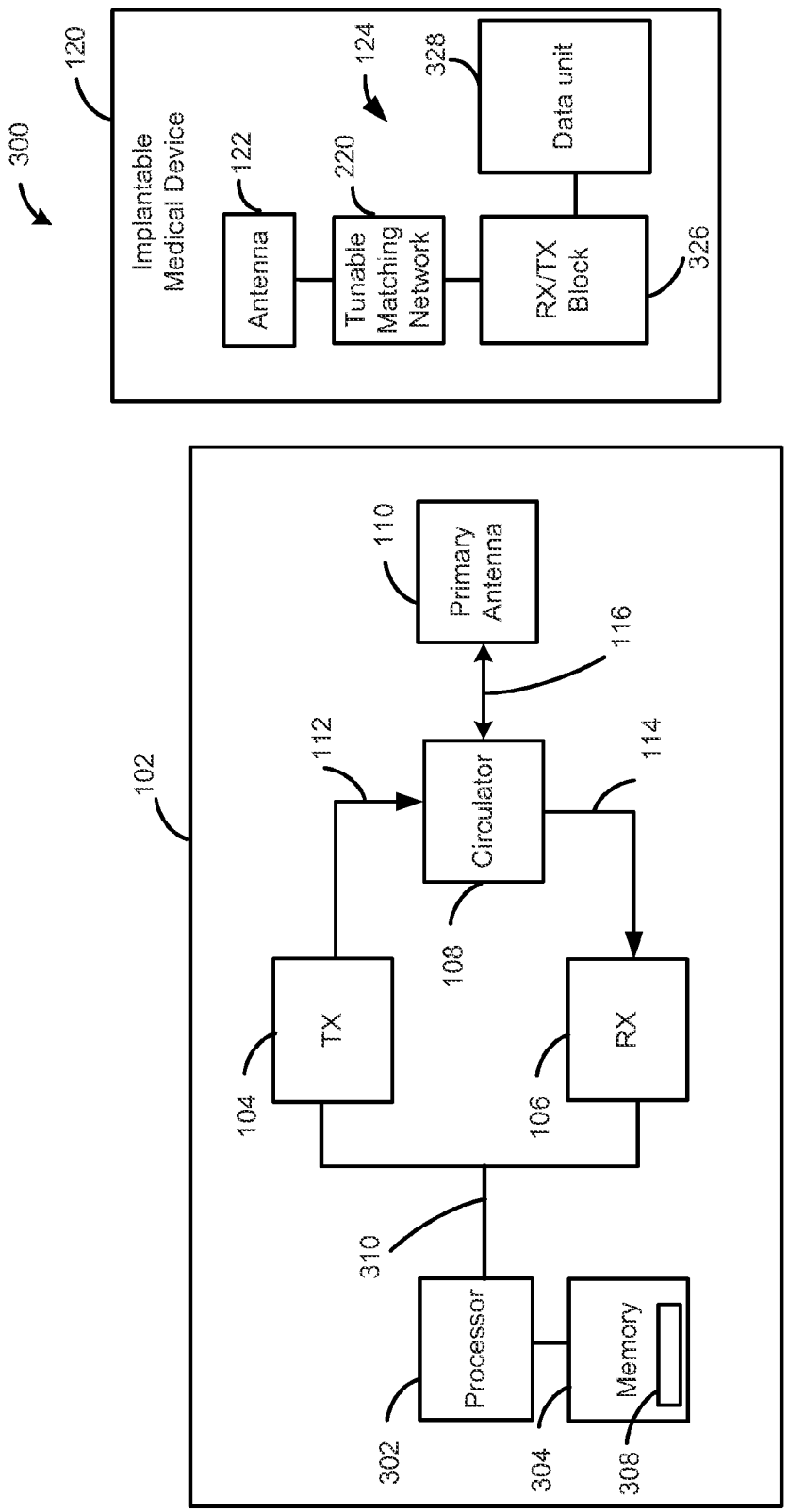
FIG. 3 is a block diagram of a system including the external device and the implantable medical device according to a third exemplary embodiment.

Referring to FIG. 3, a block diagram of a system 300 including the external device 102 and the implantable medical device (IMD) 120 is shown according to another particular embodiment. As in FIG. 2, the external device 102 includes the transmitter 104, the receiver 106, the circulator 108, the primary antenna 110, the processor 202 and the memory device 204 that includes the instructions 208.

As in FIG. 2, the IMD 120 includes the antenna 122, the tunable matching network 220, and the component 124 that is responsive to the signal. In FIG. 3, the component 124 that is responsive to the signal may include, be included within, or correspond to the tunable matching network 220, a receive/transmit (RX/TX) block 326, a data unit 328, or a combination thereof. The antenna 122 is coupled to the tunable matching network 220. The tunable matching network 220 is coupled to the RX/TX block 326. The RX/TX block 326 may include a transmitter, a receiver, or a transceiver. The RX/TX block 326 may be coupled to the data unit 328.

The data unit 328 may be configured to gather body parameter data from a body of the patient in which the IMD 120 is implanted, to gather data associated with the operation of the IMD 120 (e.g., stimulation parameters, battery life parameters, diagnostic information), to process data received by the RX/TX block 326, and/or to store or retrieve data. For example, the data unit 328 may include or be coupled to one or more sensors that gather the body parameter data. In another example, the data unit may be coupled to one or more electrodes (not shown). The body parameter data gathered by the data unit may be communicated to the external device, e.g., via the RX/TX block 326, may be stored in a memory (not shown) of the IMD 120, or both. The body parameter data may include any measurable quantity descriptive of or related to body processes, such as electrocardiogram data, electroencephalogram data, electromyography data, respiratory data (e.g., respiration rate), blood or body chemistry data (e.g., blood oxygen saturation), acceleration data, body electrical characteristics data (e.g., tissue conductivity data), other body parameters, or a combination thereof.

In a particular embodiment, the tunable matching network 220 includes one or more capacitors, one or more inductors, one or more resistors, or any combination thereof. Impedance of the tunable matching network 220 may be adjusted to reduce signal power loss due to signal reflection that may be caused by impedance mismatch between the antenna 122, the tunable matching network 220 and other components of the IMD 120, such as the RX/TX block 326 and the data unit 328. To illustrate, the impedance of the tunable matching network 220 may be adjusted to provide improved impedance matching between the antenna 122, the tunable matching network 220, and the RX/TX block 326. For example, the impedance of the tunable matching network 220 may be adjusted by adjusting a capacitance of one or more capacitors of the tunable matching network 220. Impedance mismatch may reduce charging efficiency at the charge storage element 222.

In a particular embodiment, a characteristic of the backscatter signal generated by the IMD 120 in response to the signal is related to the impedance matching between the antenna 122, the tunable matching network 220, and other components of the IMD 120. The processor 202 may be operable to determine, based on the characteristic of the backscatter signal, whether the impedance matching at the IMD 120 is within acceptable tolerances. When the impedance matching is not within acceptable tolerances, the processor 202 may cause the transmitter 104 to send a tuning signal to the IMD 120. In response to the tuning signal, the impedance of the tunable matching network 220 may be modified. Thus, the backscatter signal may be used to improve efficiency of communications between the external device 102 and the RX/TX block 326.

Alternately, or in addition, the processor 202 may cause the transmitter 104 to change a frequency of the signal, based on the backscatter signal, to reduce impedance mismatch at the IMD 120. For example, the processor 202 may cause the transmitter 104 to perform a frequency sweep of particular channels or frequency bands. The external device 102 may communicate with the IMD 120 using a selected channel of multiple available channels. The RX/TX block 326 may also or in the alternative communicate with the external device 102 using the selected channel. The available channels may correspond to frequency bands that are authorized (e.g., by an appropriate governmental agency, such as the Federal Communication Commission in the United States) for use for medical device communications or other relatively low power, short range communications. The transmitter 104 may perform the frequency sweep by transmitting a first signal to the IMD 120 using a first channel of the available channels, subsequently transmitting a second signal to the IMD 120 using a second channel of the available channels, and so forth, through each of the available channels or through a subset of the available channels.

The receiver 106 may receive a backscatter signal corresponding to each signal transmitted during the frequency sweep (e.g., a first backscatter signal corresponding the first signal, a second backscatter signal corresponding the second signal, and so forth). The receiver 106 or the processor 202 may select a particular channel to be used to communicate with the IMD 120 (e.g., to send data to the IMD 120, to receive data from the IMD 120, or both) based on the backscatter signals received during the frequency sweep. For example, a channel that corresponds to a backscatter signal that had a largest amplitude (e.g., a highest power backscatter signal) may be selected.

As explained above, the receiver 106 may receive a leakage signal corresponding to each signal transmitted during the frequency sweep. Thus, a signal detected may include the backscatter signal and the leakage signal. In this circumstance, the receiver 106 or the processor 202 may select a particular channel to be used to communicate with the IMD 120 that had a largest difference in amplitude between the backscatter signal and the leakage signal.

Use of the backscatter signal to extract and/or estimate information about the IMD 120 may enable determination of the information without the IMD 120 using stored energy to generate and to send a radiofrequency signal to convey the information about the IMD 120 to the external device 102. Thus, use of the backscatter signal may substantially reduce power consumption associated with generating and sending a signal to the external device 102 to convey the information about the IMD 120.

Although FIG. 3 shows the processor 202 and the memory device 204 as part of the external device 102, in alternative embodiments, one or both of the processor 202 and the memory device 204 may be outside the external device 102. In addition, although FIG. 3 shows the tunable matching network 220 outside the RX/TX block 326, in alternative embodiments, the tunable matching network 220 may be inside the RX/TX block 326.

Figure 4:
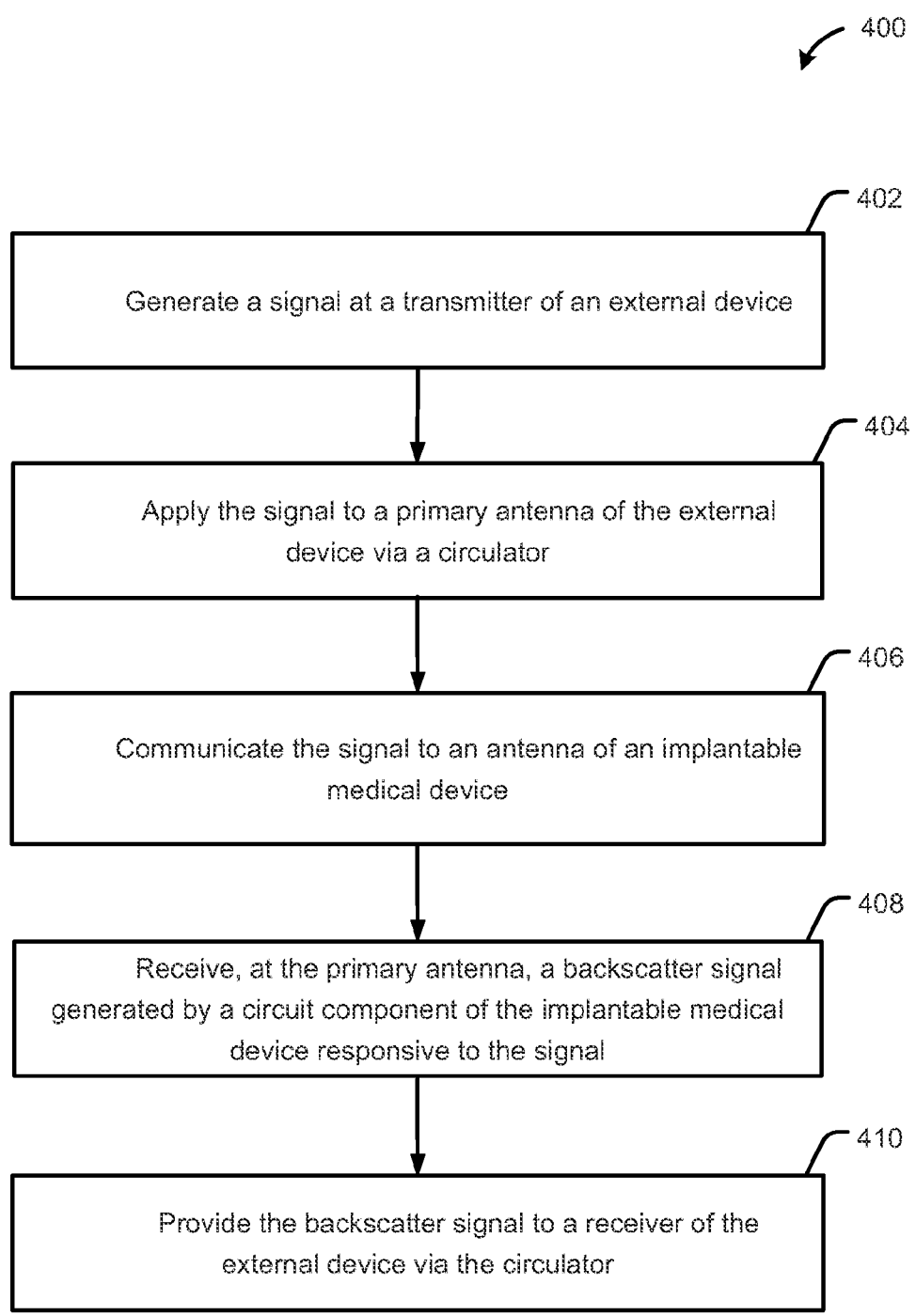
FIG. 4 is a flow chart of a method of generating a signal and receiving a backscatter signal according to a first particular embodiment.

Referring to FIG. 4, a flow chart of a method of generating a signal and receiving a backscatter signal according to an exemplary embodiment is shown and generally designated 400. The method 400 may include generating a signal at a transmitter of an external device, at 402. For example, the transmitter 104 of FIG. 1, 2 or 3 may generate the signal. The signal may be a charging signal (i.e., a signal used to charge a charge storage element of an implantable medical device), a communication signal, or a combination thereof. The method 400 also includes applying the signal to a primary antenna of the external device via a circulator, at 404. For example, the transmitter 104 may send the signal to the primary antenna 110 via the circulator 108, as shown in FIGS. 1, 2 and 3. The method 400 may further include communicating the signal to an antenna of the implantable medical device, at 406. For example, the primary antenna 110 may radiate the signal as a radiofrequency (RF), far-field signal. The implantable medical device (IMD) may include a circuit component that is responsive to the signal. For example, the IMD 120 of FIG. 1 includes the component 124 that is responsive to the signal.

The method 400 may include receiving, at the primary antenna, a backscatter signal generated by the component of the implantable medical device that is responsive to the signal, at 408. For example, the primary antenna 110 may receive the backscatter signal from the antenna 122 of the IMD 120. The backscatter signal may have the same frequency as the signal transmitted by the external device. The method 400 may also include providing the backscatter signal to a receiver of the external device via the circulator, at 410. For example, the primary antenna 110 may provide the backscatter signal to the receiver 106 via the circulator 108, as shown in FIGS. 1, 2 and 3. The circulator enables concurrent or simultaneous transmission of the signal and reception of the backscatter signal at a single frequency by the external device.

Figure 5:
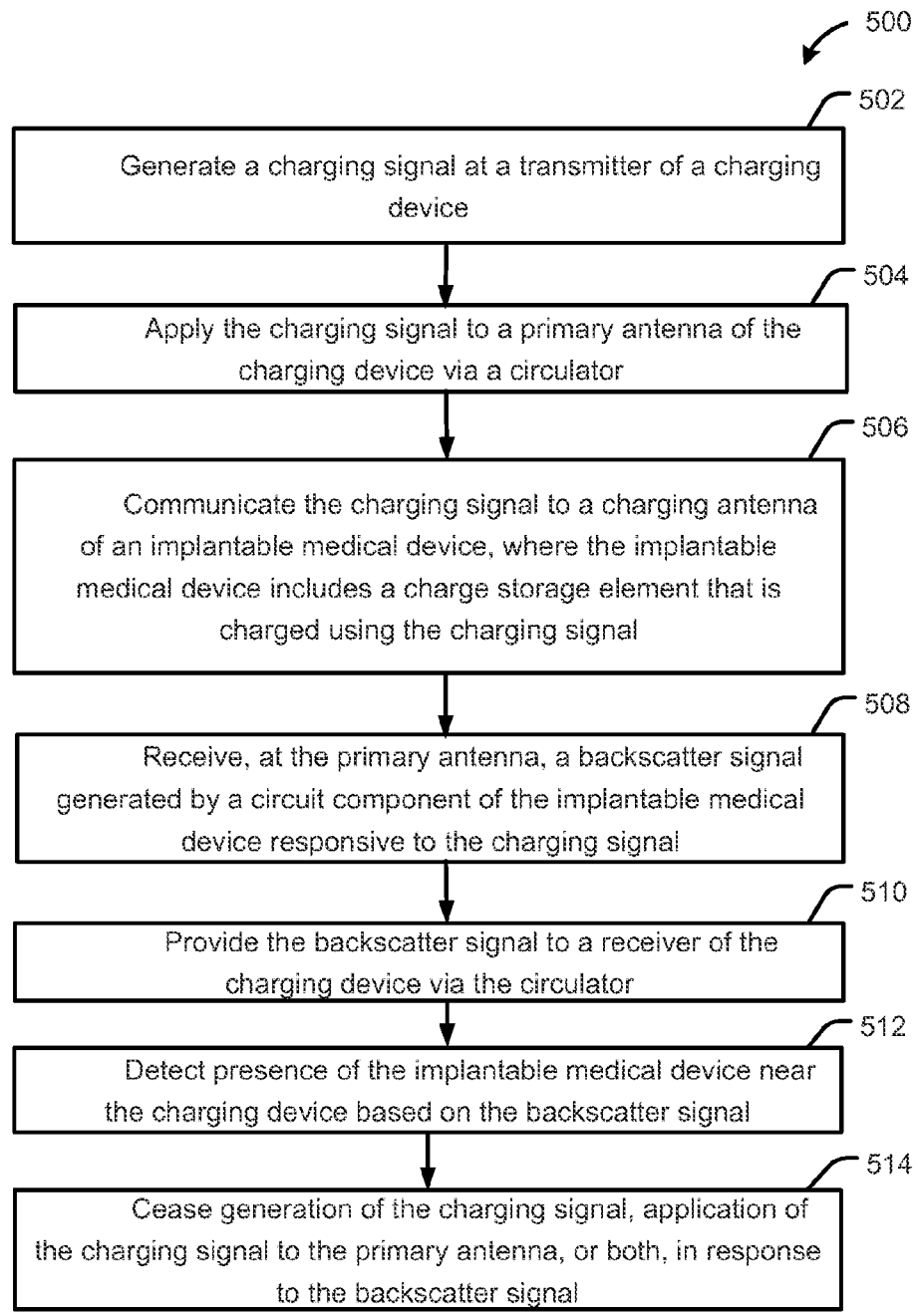
FIG. 5 is a flow chart of a method of generating a signal and receiving a backscatter signal according to a second particular embodiment.

Referring to FIG. 5, a flow chart of a method of generating a charging signal and receiving a backscatter signal according to an exemplary embodiment is shown and generally designated 500. The method 500 may include generating a charging signal at a transmitter of a charging device, at 502. The charging device may be an external device, such as the external device 120 of FIG. 2, that transmits a charging signal to an implantable medical device. For example, the transmitter 104 of FIG. 2 may generate the charging signal. The method 500 also includes applying the charging signal to a primary antenna of the charging device via a circulator, at 504. For example, the transmitter 104 may send the charging signal to the primary antenna 110 via the circulator 108, as shown in FIG. 2. The method 500 may further include communicating the charging signal to an antenna of the implantable medical device, at 506. For example, the primary antenna 110 may radiatively send the charging signal to the antenna 122, as shown in FIG. 2. The implantable medical device (IMD) may include a charge storage element that is charged using the charging signal. For example, the IMD 120 of FIG. 2 includes the charge storage element 222 that is charged based on the charging signal. In a particular embodiment, the IMD may provide therapy to a patient using power from the charge storage element.

The method 500 may include receiving, at the primary antenna, a backscatter signal generated by a component of the implantable medical device responsive to the charging signal, at 508. For example, the primary antenna 110 may receive the backscatter signal from the antenna 122 of the IMD 120. The backscatter signal may have the same frequency as the charging signal. The method 500 may also include providing the backscatter signal to a receiver of the charging device via the circulator, at 510. For example, the primary antenna 110 may provide the backscatter signal to the receiver 106 via the circulator 108, as shown in FIG. 2.

The method 500 may include detecting presence of the implantable medical device near (e.g., with a communication range of) the charging device based on the backscatter signal, at 512. For example, the processor 202 of FIG. 2 may detect the presence of the IMD 120 based on the backscatter signal from the IMD 120.

The method 500 may include ceasing generation of the charging signal, ceasing application of the charging signal to the primary antenna, or both, in response to detecting a condition indicated by the backscatter signal, at 514. For example, the processor 202 may send a control signal to the transmitter 104 to instruct the transmitter 104 to cease generation of the charging signal, to cease sending the charging signal to the primary antenna 110, or both in response to the backscatter signal. The transmitter 104 may cease generation of the charging signal, cease sending the charging signal to the primary antenna 110, or both based on the control signal from the processor 202. For example, the transmitter 104 may be directed to cease sending the charging signal when the charge storage element achieves a particular charge state or to avoid excess heating of the IMD 120. In another example, the transmitter 104 may be directed to cease sending the charging signal when the backscatter signal is not received for a particular period of time while the charging signal is being sent. To illustrate, failure to receive the backscatter signal may indicate that the IMD is out of range of the charging signal.

Figure 6:
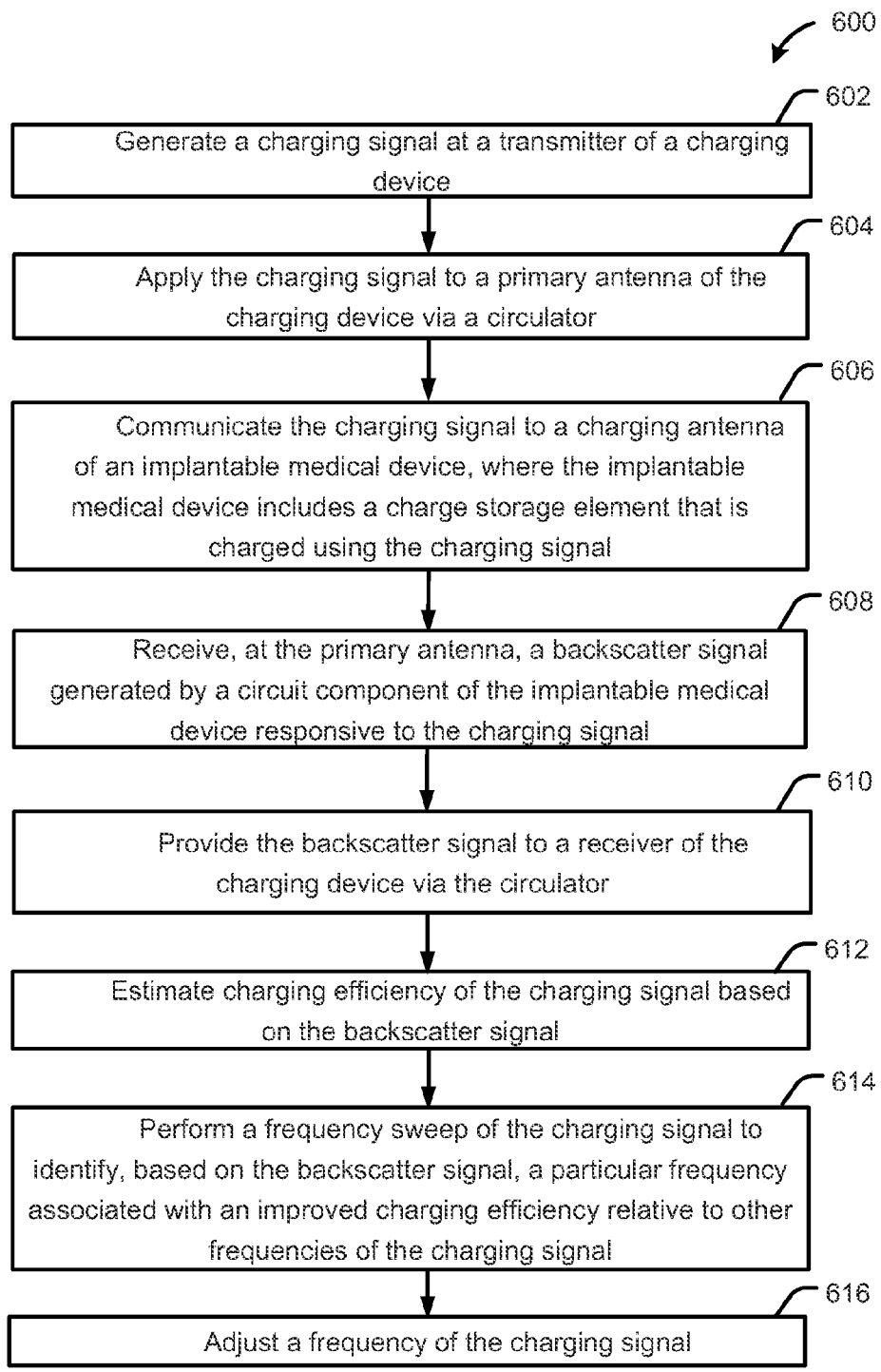
FIG. 6 is a flow chart of a method of generating a signal and receiving a backscatter signal according to a third particular embodiment.

Referring to FIG. 6, a flow chart of a method of generating a charging signal and receiving a backscatter signal according to an exemplary embodiment is shown and generally designated 600. The method 600 may include generating a charging signal at a transmitter of a charging device, at 602. The charging device may be an external device, such as the external device 120 of FIG. 2, that transmits a charging signal to an implantable medical device. For example, the transmitter 104 of FIG. 2 may generate the charging signal. The method 600 also includes applying the charging signal to a primary antenna of the charging device via a circulator, at 604. For example, the transmitter 104 may send the charging signal to the primary antenna 110 via the circulator 108, as shown in FIG. 2. The method 600 may further include communicating the charging signal to a charging antenna of the implantable medical device, at 606. For example, the primary antenna 110 may radiatively send the charging signal to the antenna 122, as shown in FIG. 2. The implantable medical device (IMD) may include a charge storage element that is charged using the charging signal. For example, the IMD 120 of FIG. 2 includes the charge storage element 222 that is charged based on the charging signal. In a particular embodiment, the IMD may provide therapy to a patient using power from the charge storage element.

The method 600 may include receiving, at the primary antenna, a backscatter signal generated by a component of the implantable medical device responsive to the charging signal, at 608. For example, the primary antenna 110 may receive the backscatter signal from the antenna 122 of the IMD 120. The backscatter signal may have the same frequency as the charging signal. The method 600 may also include providing the backscatter signal to a receiver of the charging device via the circulator, at 610. For example, the primary antenna 110 may provide the backscatter signal to the receiver 106 via the circulator 108, as shown in FIG. 2.

The method 600 may include estimating charging efficiency of the charging signal based on the backscatter signal, 612. For example, the processor 202 of FIG. 2 may estimate the charging efficiency of the charging signal based on a characteristic of the backscatter signal. The method 600 may also include performing a frequency sweep of the charging signal to identify, based on the backscatter signal, a particular frequency associated with an improved charging efficiency relative to other frequencies of the charging signal, at 614. To illustrate, the processor 202 may repeatedly send a control signal to the transmitter 104 instructing the transmitter 104 to change the frequency of the charging signal. The processor 202 may process the backscatter signal for each frequency of the charging signal to identify a particular frequency associated with an improved charging efficiency.

The method 600 may include adjusting a frequency of the charging signal, at 616. For example, the processor 202 may send a control signal to the transmitter 104 instructing the transmitter 104 to change the frequency of the charging signal. To illustrate, the processor 202 may send the control signal to the transmitter 104 instructing the transmitter 104 to change the frequency of the charging signal after estimating the charging efficiency of the charging signal. The processor 202 may also send the control signal to the transmitter 104 after identifying a particular frequency associated with an improved charging efficiency.

Figure 7:
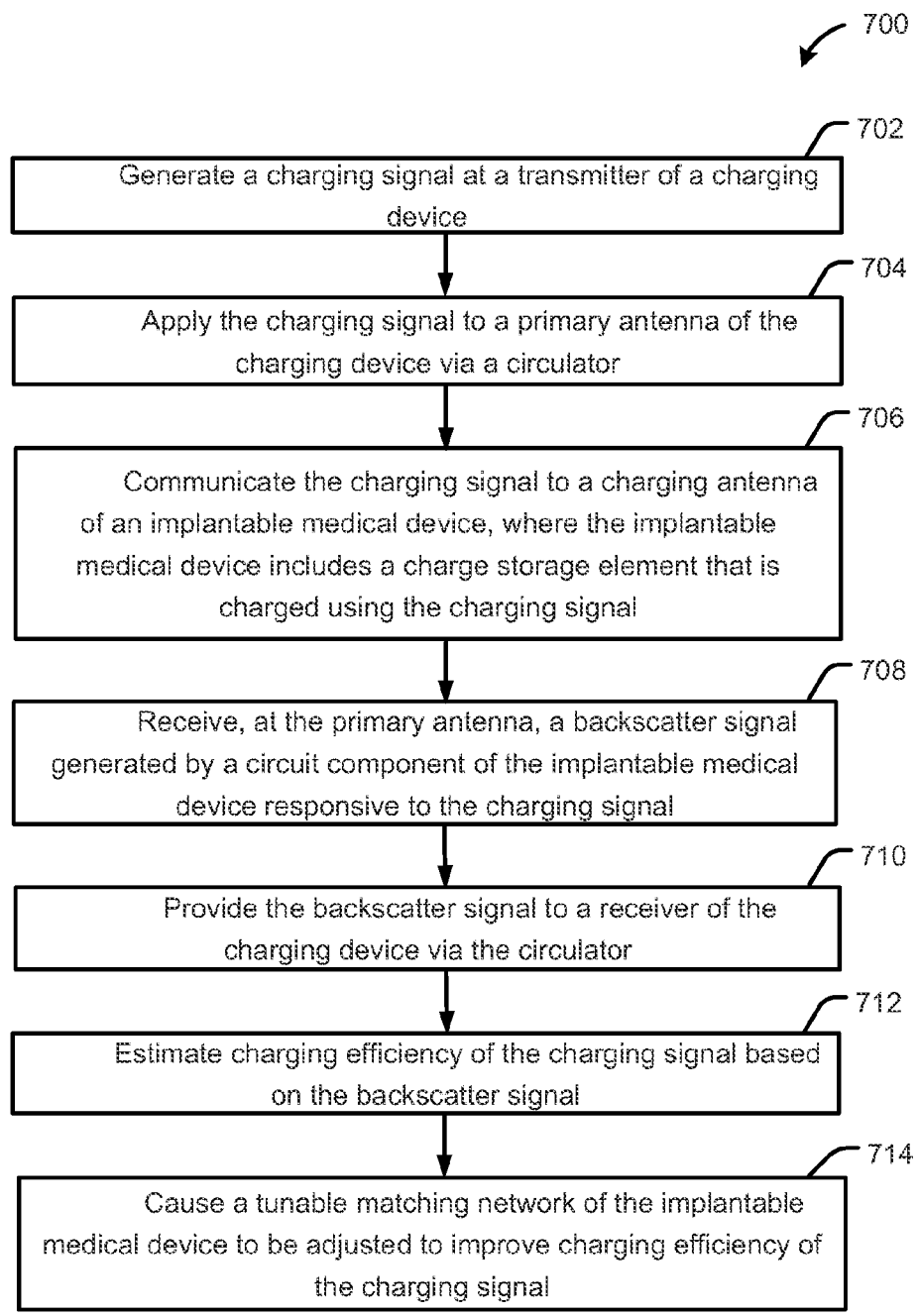
FIG. 7 is a flow chart of a method of generating a signal and receiving a backscatter signal according to a fourth particular embodiment.

Referring to FIG. 7, a flow chart of a method of generating a charging signal and receiving a backscatter signal according to an exemplary embodiment is shown and generally designated 700. The method 700 may include generating a charging signal at a transmitter of a charging device, at 702. The charging device may be an external device, such as the external device 120 of FIG. 2, that transmits a charging signal to an implantable medical device. For example, the transmitter 104 of FIG. 2 may generate the charging signal. The method 700 also includes applying the first signal to a primary antenna of the charging device via a circulator, at 704. For example, the transmitter 104 may send the charging signal to the primary antenna 110 via the circulator 108, as shown in FIG. 2. The method 700 may further include communicating the charging signal to an antenna of an implantable medical device, at 706. For example, the primary antenna 110 may radiatively send the charging signal to the antenna 122, as shown in FIG. 2. The implantable medical device (IMD) may include a charge storage element that is charged using the charging signal. For example, the IMD 120 of FIG. 2 includes the charge storage element 222 that is charged based on the charging signal. In a particular embodiment, the IMD may provide therapy to a patient using power from the charge storage element.

The method 700 may include receiving, at the primary antenna, a backscatter signal generated by a component of the implantable medical device responsive to the charging signal, at 708. For example, the primary antenna 110 may receive the backscatter signal from the antenna 122 of the IMD 120. The backscatter signal may have the same frequency as the charging signal. The method 700 may also include providing the backscatter signal to a receiver of the charging device via the circulator, at 710. For example, the primary antenna 110 may provide the backscatter signal to the receiver 106 via the circulator 108, as shown in FIG. 2.

The method 700 may include estimating charging efficiency of the charging signal based on the backscatter signal, 712. For example, the processor 202 of FIG. 2 may estimate the charging efficiency of the charging signal based on a characteristic of the backscatter signal. The method 700 may also include causing a tunable matching network of the implantable medical device to be adjusted to improve charging efficiency of the charging signal, at 714. For example, after estimating the charging efficiency of the charging signal, the processor 202 may generate an output signal to indicate whether impedance of the tunable matching network 220 of the IMD 120 in FIG. 2 should be increased, decreased, or maintained.

Figure 8:
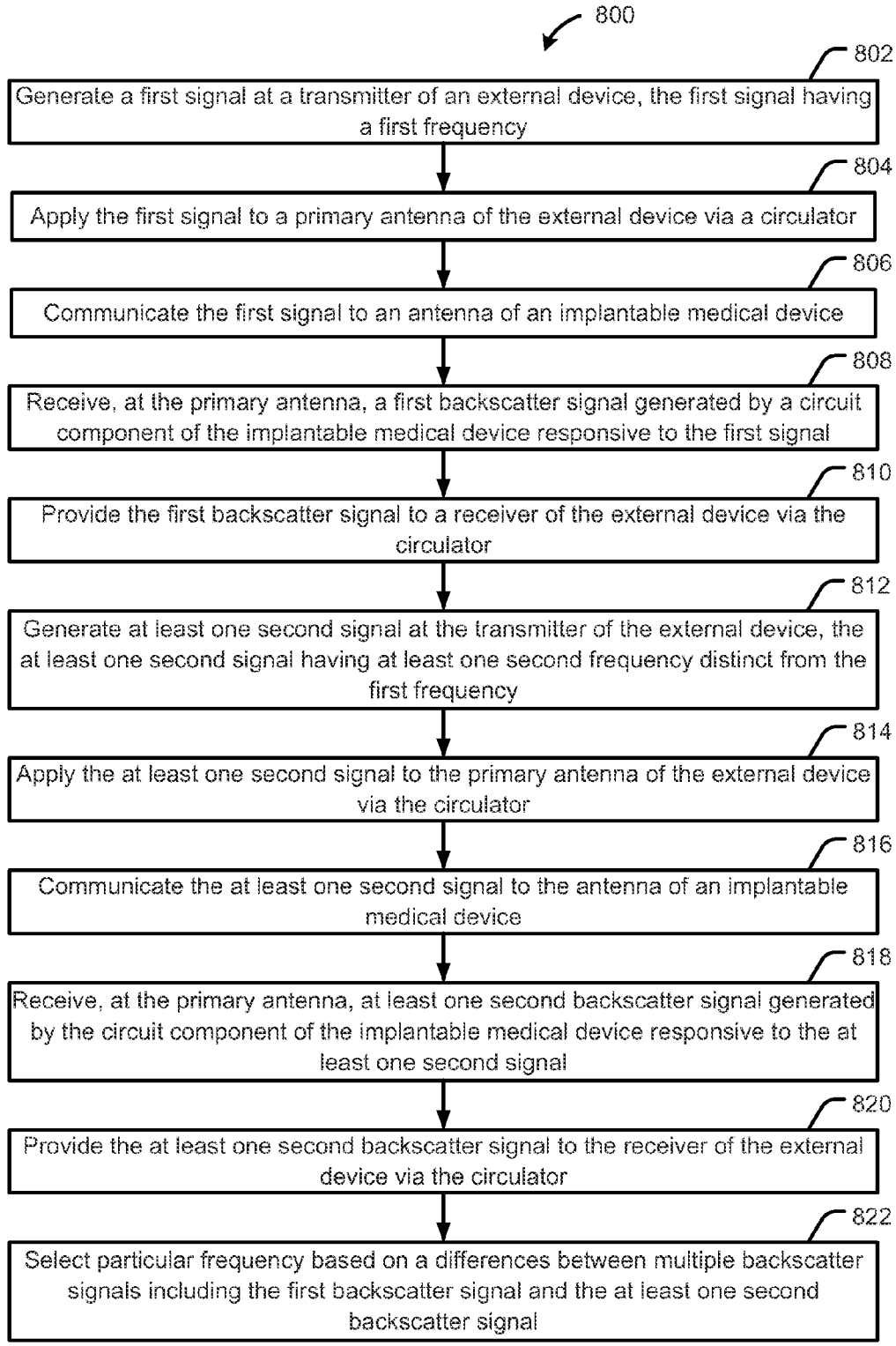
FIG. 8 is a flow chart of a method of generating a signal and receiving a backscatter signal according to a fifth particular embodiment.

Referring to FIG. 8, a flow chart of a method of performing a frequency sweep to select a frequency based on a backscatter signal according to an exemplary embodiment is shown and generally designated 800. The method 800 may include generating a first signal at a transmitter of an external device, the first signal having a first frequency, at 802. For example, the transmitter 104 of FIGS. 1-3 may generate the first signal. The method 800 may also include applying the first signal to a primary antenna of the external device via a circulator, at 804. For example, the transmitter 104 may send the charging signal to the primary antenna 110 via the circulator 108, as shown in FIGS. 1-3. The method 800 may further include communicating the first signal to an antenna of an implantable medical device, at 806. For example, the primary antenna 110 may radiatively send the first signal to the antenna 122, as shown in FIGS. 1-3. The first signal may include a charging signal that is used to charge a charge storage element of the implantable medical device (IMD). Alternately or in addition, the first signal may include a communication signal used to transmit a command or data to the IMD. In another alternative embodiment, the first signal may be a test signal that is used to select a frequency to be used for other purposes, such as charging or communication.

The method 800 may include receiving, at the primary antenna, a first backscatter signal generated by a component of the implantable medical device responsive to the first signal, at 808. For example, the primary antenna 110 may receive the first backscatter signal from the antenna 122 of the IMD 120. The first backscatter signal may have the same frequency as the first signal. The method 800 may also include providing the first backscatter signal to a receiver of the external device via the circulator, at 810. For example, the primary antenna 110 may provide the first backscatter signal to the receiver 106 via the circulator 108, as shown in FIGS. 1-3.

The method 800 may include generating at least one second signal at the transmitter, at 812. The at least one second signal may have at least one second frequency that is distinct from the first frequency of the first signal. The at least one second signal may include multiple signals, each corresponding to a different communication channel. For example, the transmitter 104 of FIGS. 1-3 may generate the at least one second signal after generating the first signal in response to a command from a processor to perform a frequency sweep. The method 800 may also include applying at least one second signal to the primary antenna of the external device via the circulator, at 814. For example, when the at least one second signal includes only one second signal, the transmitter 104 may send the second signal to the primary antenna 110 via the circulator 108, as shown in FIGS. 1-3. When the at least one second signal includes multiple second signals, the multiple second signals may be sent to the primary antenna 110 via the circulator 108 one at a time, allowing time for the receiver 106 to receive a backscatter signal corresponding to each signal before proceeding to send a subsequent signal.

The method 800 may further include communicating at least one second signal to the antenna of the implantable medical device, at 816. For example, the primary antenna 110 may radiatively send at least one second signal to the antenna 122, as shown in FIGS. 1-3. Like the first signal, the at least one second signal may include a charging signal, a communication signal, another signal, or a combination thereof.

The method 800 may include receiving, at the primary antenna, at least one second backscatter signal generated by a component of the implantable medical device responsive to the at least one second signal, at 818. For example, a backscatter signal corresponding to each of multiple second signals may be received when the at least one second signal includes multiple second signals. To illustrate, the primary antenna 110 may receive at least one second backscatter signal from the antenna 122 of the IMD 120. Each of the at least one second backscatter signals may have the same frequency as a corresponding one of the at least one second signals. The method 800 may also include providing at least one second backscatter signal to a receiver of the external device via the circulator, at 820. For example, the primary antenna 110 may provide the second backscatter signal to the receiver 106 via the circulator 108, as shown in FIGS. 1-3.

The method 800 may also include selecting a particular frequency (or channel) based on a differences between multiple backscatter signals including the first backscatter signal and the at least one second backscatter signal, at 822. For example, the processor 202 of FIGS. 2 and 3 may select a frequency (or channel) that will be used for charging the IMD or that will be used to communicate with the IMD based on the multiple backscatter signals. To illustrate, a frequency (or channel) corresponding to a largest amplitude backscatter signal of the multiple backscatter signals may be selected. In another illustrative example, a frequency (or channel) corresponding to a largest amplitude difference between a backscatter signal of the multiple backscatter signals and a corresponding leakage signal may be selected. The transmitter of the external device may be tuned to the selected frequency (or channel) for subsequent communications with or charging of the IMD.

Figure 9:
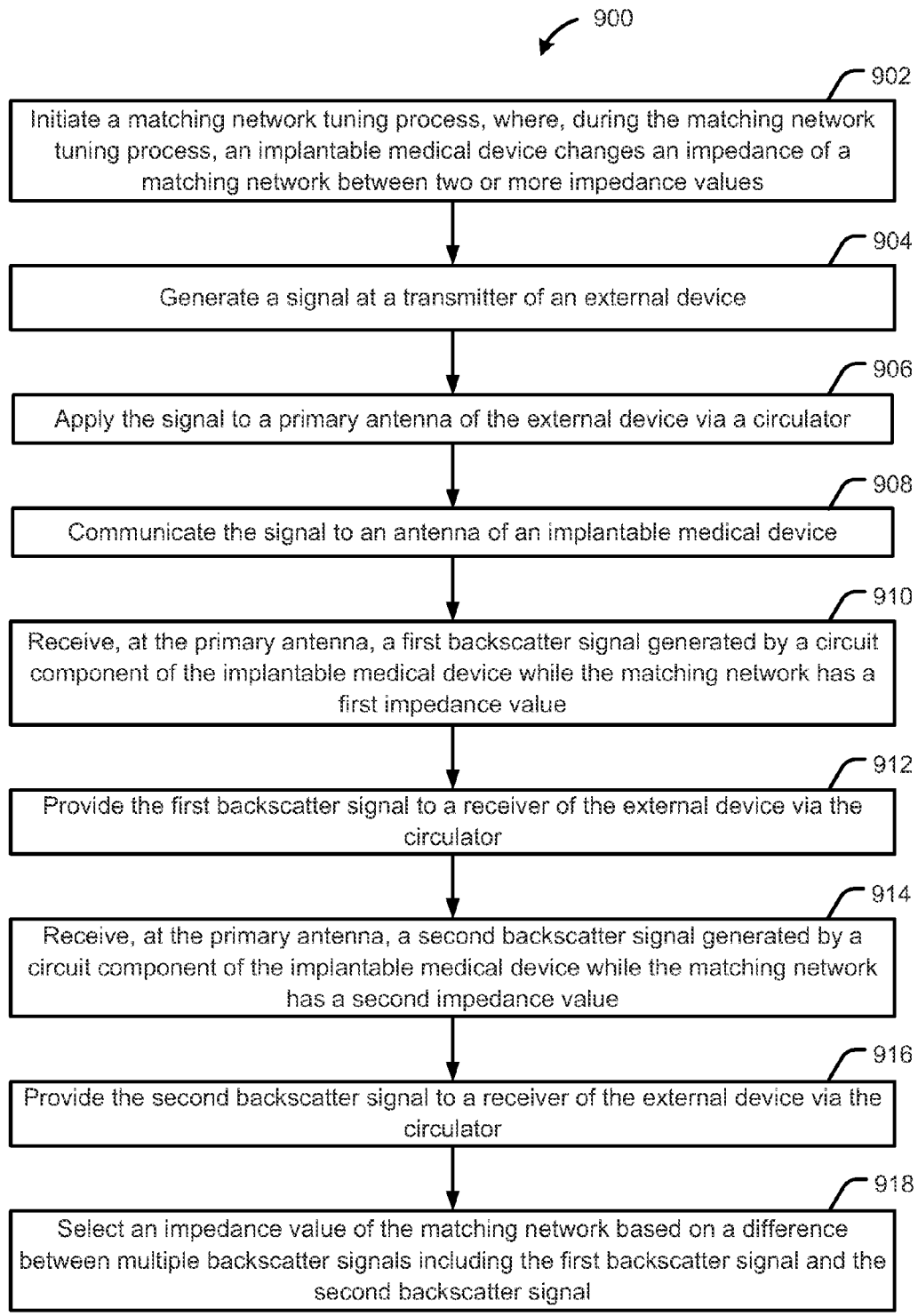
FIG. 9 is a flow chart of a method of generating a signal and receiving a backscatter signal according to a sixth particular embodiment.

Referring to FIG. 9, a flow chart of a method of tuning a matching network based on a backscatter signal according to an exemplary embodiment is shown and generally designated 900. The method 900 may include initiating a matching network tuning process, at 902. For example, the tunable matching network 220 of FIGS. 2 and 3 may begin the matching network tuning process in response to a command from the external device 102. During the matching network tuning process, an implantable medical device changes an impedance of the matching network between two or more impedance values. For example, an impedance value of the tunable matching network 220 of FIGS. 2 and 3 may be adjusted one or more times to different impedance values by the IMD 120.

The method 900 may also include generating a signal at a transmitter of an external device, at 904. For example, the transmitter 104 of FIGS. 1-3 may generate the signal. The method 900 may also include applying the signal to a primary antenna of the external device via a circulator, at 906. For example, the transmitter 104 may send the signal to the primary antenna 110 via the circulator 108, as shown in FIGS. 1-3. The method 900 may further include communicating the signal to an antenna of an implantable medical device, at 908. For example, the primary antenna 110 may radiatively send the signal to the antenna 122, as shown in FIGS. 1-3. The signal may include a charging signal that is used to charge a charge storage element of the implantable medical device (IMD). Alternately or in addition, the signal may include a communication signal used to transmit a command or data to the IMD. In another alternative embodiment, the signal may be a test signal that is used in connection with the matching network tuning process. The method 900 may include receiving, at the primary antenna, a first backscatter signal generated by a component of the implantable medical device responsive to the signal while the matching network has a first impedance value, at 910. For example, the primary antenna 110 may receive the first backscatter signal from the antenna 122 of the IMD 120 while the tunable matching network 220 has a first impedance value. The method 900 may also include providing the first backscatter signal to a receiver of the external device via the circulator, at 912. For example, the primary antenna 110 may provide the first backscatter signal to the receiver 106 via the circulator 108, as shown in FIGS. 1-3.

The method 900 may include receiving, at the primary antenna, a second backscatter signal generated by the component of the implantable medical device responsive to the signal while the matching network has a second impedance value, at 914. For example, the primary antenna 110 may receive the second backscatter signal from the antenna 122 of the IMD 120 while the tunable matching network 220 has a second impedance value. The method 900 may also include providing the second backscatter signal to the receiver of the external device via the circulator, at 916. For example, the primary antenna 110 may provide the second backscatter signal to the receiver 106 via the circulator 108, as shown in FIGS. 1-3.

Although not specifically shown in FIG. 9, the method 900 may include receiving one or more additional backscatter signals corresponding to one or more other impedance values of the matching network. For example, the matching network may cycle through more than two impedance values and a backscatter signal corresponding to each impedance value may be received at the external device. In another example, rather than tuning the matching network from one discrete value to another discrete value, the matching network may be tuned over a continuum of impedance values. In this example, the first and second backscatter signals may correspond to particular portions of a continuous backscatter signal that has one or more parameters that change over time as the impedance value of the matching network changes.

The method 900 may also include selecting an impedance value of the matching network based on a difference between multiple backscatter signals including the first backscatter signal and the second backscatter signal, at 918. For example, the processor 202 of FIGS. 2 and 3 may select the impedance value for the tunable matching network 220. In this example, the processor 202 may send a command signal to the IMD 120 to cause the IMD 120 to adjust the tunable matching network 220 to have the selected impedance value. The selected impedance value may correspond to a largest amplitude backscatter signal of the multiple backscatter signals. In another illustrative example, the selected impedance value may correspond to a largest amplitude difference between a backscatter signal of the multiple backscatter signals and a corresponding leakage signal may be selected.

As illustrated by the described embodiments, an apparatus is disclosed that may include means for generating the charging signal at a charging device. For example, the means for generating a charging signal may include the transmitter 104 of FIGS. 1-3. The apparatus may also include means for applying the charging signal to a charging antenna of an implantable medical device by inductive coupling to the charging antenna, where the implantable medical device includes a charge storage element that is charged using the charging signal. For example, the means for applying the charging signal may include the primary antenna 110 of FIGS. 1-3. The apparatus may further include means for receiving a backscatter signal generated by a component of the implantable medical device responsive to the charging signal. For example, the means for receiving a backscatter signal may include the receiver 106 of FIGS. 1-3. The apparatus may also include means for processing the backscatter signal. For example, the means for processing the backscatter signal may include the processor 202 of FIG. 2. The apparatus may include means for estimating a depth of the implantable medical device within tissue of a patient based on the backscatter signal. For example, the processor 202, or a processor external to the external device 102, may estimate the depth of the implantable medical device within tissue of a patient based on the backscatter signal.

Although the description above contains many specificities, these specificities are utilized to illustrate some particular embodiments of the disclosure and should not be construed as limiting the scope of the disclosure. The scope of this disclosure should be determined by the claims, their legal equivalents and that the disclosure encompasses other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments of the systems and methods and programs of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, a special purpose computer processor, or by a hardwired system.

As noted above, embodiments within the scope of the present disclosure include program products including machine-readable media for carrying or having machine-executable instructions or data structures stored thereon. Such machine-readable media can be any available media which can be accessed by a general purpose or special purpose computer or other machine with a processor. By way of example, such machine-readable media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, a special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure.

The foregoing description of embodiments of the disclosure has been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:
1. A device comprising:
a primary antenna configured to transmit a signal to an antenna of an implantable medical device (IMD) and to receive a backscatter signal from the IMD, wherein the backscatter signal is a reflection of the signal transmitted from the primary antenna;

a circulator coupled to the primary antenna, wherein the circulator is configured to route the signal from a transmitter to the primary antenna, to route the backscatter signal from the primary antenna to a receiver, and to allow a portion of the signal to pass to the receiver as a leakage signal; and a processor coupled to the receiver, the processor configured to determine, based at least partially on a difference in amplitude between the backscatter signal received from the IMD via the primary antenna and the leakage signal, an updated frequency for the signal transmitted to the IMD via the primary antenna, wherein the processor is configured to perform a sweep of the signal across a range of frequencies and to monitor the backscatter signal for each frequency of the sweep to determine the updated frequency.

2. The device of claim 1, wherein the backscatter signal has the same frequency as the signal.

3. The device of claim 1, wherein at least one component of the IMD is part of a tunable matching network, wherein the processor is configured to send a control signal to the transmitter, wherein the transmitter is configured to send a tuning signal to the IMD via the primary antenna, and wherein the tuning signal is configured to cause an impedance of the at least one component of the tunable matching network to be adjusted to an updated impedance value responsive to the backscatter signal.

4. The device of claim 1, wherein the processor is configured to send a control signal to the transmitter, wherein the transmitter is configured to send a tuning signal to the IMD, and wherein the tuning signal is configured to cause an impedance of at least one component of the IMD to be adjusted to a plurality of impedance values and to monitor the backscatter signal for each impedance value of the plurality of impedance values to determine an updated impedance value.

5. The device of claim 1, wherein the processor is configured to send a control signal to the transmitter, wherein the transmitter is configured to adjust a frequency of the signal to the updated frequency responsive to the backscatter signal.

6. The device of claim 1, wherein the signal corresponds to a charging signal configured to charge a charge storage element of the IMD.

7. The device of claim 6, wherein the processor is configured to estimate, based on the backscatter signal, charging efficiency of the charging signal with respect to the charge storage element.

8. The device of claim 1, wherein the signal is a communication signal, and wherein the primary antenna is configured to communicate with a receive/transmit block of the IMD.

9. The device of claim 1, wherein the processor is configured to:
identify a frequency at which the difference in amplitude between the backscatter signal and the leakage signal is largest from among the frequencies of the sweep; and
set the frequency at which the difference in amplitude between the backscatter signal and the leakage signal is the largest as the updated frequency.

10. A method comprising:
generating a signal at a transmitter of a device;
transmitting, via a primary antenna of the device, the signal to an antenna of an implantable medical device (IMD), wherein the signal is provided to the primary antenna via a circulator of the device;

passing, via the circulator, a portion of the signal to a receiver of the device as a leakage signal;
receiving, via the primary antenna, a backscatter signal from the IMD, wherein the backscatter signal is provided to the receiver via the circulator, wherein the backscatter signal is a reflection of the signal transmitted from the primary antenna;
performing, via a processor, a sweep of the signal across a range of frequencies;
monitoring, via the processor, the backscatter signal for each frequency of the sweep; and
determining, based at least partially on a difference in amplitude between the backscatter signal monitored during the sweep and the leakage signal, an updated frequency for the signal transmitted to the IMD.

11. The method of claim 10, further comprising estimating communication efficiency of the signal based on the backscatter signal.

12. The method of claim 11, wherein the signal corresponds to a charging signal configured to charge a charge storage element of the IMD, and wherein the communication efficiency of the charging signal corresponds to charging efficiency of the charging signal with respect to the charge storage element.

13. The method of claim 11, further comprising, after estimating the communication efficiency, adjusting a frequency of the signal.

14. The method of claim 11, further comprising, after estimating the communication efficiency, causing a tunable matching network of the IMD to be adjusted to update an impedance of the tunable matching network according to an updated impedance value, wherein a first impedance value of the tunable matching network is associated with a first communication efficiency and the updated impedance value is associated with a second communication efficiency, and wherein the first communication efficiency is less than the second communication efficiency.

15. The method of claim 10, wherein transmitting the signal and receiving the backscatter signal are performed concurrently.

16. The method of claim 10, wherein the circulator includes a first port, a second port, and a third port, and further comprising:
providing the signal from the transmitter to the first port;
providing the signal from the first port to the primary antenna via the second port;
providing the backscatter signal from the primary antenna to the second port; and
providing the backscatter signal from the second port to the receiver via the third port.

17. The method of claim 10, wherein:
monitoring the backscatter signal comprises identifying a frequency at which the difference in amplitude between the backscatter signal and the leakage signal is largest from among the frequencies of the sweep; and
determining the updated frequency comprises setting the frequency at which the difference in amplitude between the backscatter signal and the leakage signal is the largest as the updated frequency.

18. An apparatus comprising:
means for transmitting a signal and receiving a backscatter signal, wherein the signal is transmitted to an implantable medical device (IMD), wherein the backscatter signal is a reflection of the signal transmitted from the primary antenna, and wherein the backscatter signal is received from the IMD, the means for transmitting and receiving comprising means for performing a sweep of the signal across a range of frequencies;

means for routing the signal from a transmitter to the means for transmitting and receiving, routing the backscatter signal from the means for transmitting and receiving to a receiver, and allowing a portion of the signal to pass to the receiver as a leakage signal; and means for processing the backscatter signal and determining, based at least partially on a difference in amplitude between the backscatter signal monitored during the sweep and the leakage signal, an updated frequency for the signal transmitted to the IMD.

19. The apparatus of claim 18, further comprising means for routing the signal from a transmitter to the means for transmitting and receiving and routing the backscatter signal from the means for transmitting and receiving to a receiver, wherein the signal is at least one of a charging signal configured to charge a charge storage element of the IMD or a communication signal configured to communicate with a receive/transmit block of the IMD.

20. The apparatus of claim 18, wherein the means for processing comprises:

means for identifying a frequency at which the difference in amplitude between the backscatter signal and the leakage signal is largest from among the frequencies of the sweep; and means for setting the frequency at which the difference in amplitude between the backscatter signal and the leakage signal is the largest as the updated frequency.

\* \* \* \* \*